(12) United States Patent
Yamada et al.

(10) Patent No.: US 9,459,220 B2
(45) Date of Patent: Oct. 4, 2016

(54) ALLOYED POSITION DETERMINING METHOD, ALLOYED POSITION DETERMINING APPARATUS, AND RECORDING MEDIUM

(75) Inventors: Hirohisa Yamada, Tokyo (JP); Masato Sugiura, Tokyo (JP); Satoshi Suzuki, Tokyo (JP)

(73) Assignee: NIPPON STEEL & SUMITOMO METAL CORPORATION, Tokyo (JP)

(*) Notice: Subject to any disclaimer, the term of this patent is extended or adjusted under 35 U.S.C. 154(b) by 302 days.

(21) Appl. No.: 14/240,076

(22) PCT Filed: Aug. 26, 2011

(86) PCT No.: PCT/JP2011/069323
§ 371 (c)(1),
(2), (4) Date: Feb. 21, 2014

(87) PCT Pub. No.: WO2013/030904
PCT Pub. Date: Mar. 7, 2013

(65) Prior Publication Data
US 2014/0185650 A1  Jul. 3, 2014

(51) Int. Cl.
*G01J 5/00* (2006.01)
*G01N 25/00* (2006.01)
(Continued)

(52) U.S. Cl.
CPC .............. *G01N 25/00* (2013.01); *C23C 2/06* (2013.01); *C23C 2/28* (2013.01); *G01J 5/0003* (2013.01); *G01J 5/0022* (2013.01); *G01J 2005/0029* (2013.01)

(58) Field of Classification Search
CPC ............ G01J 2005/029; G01J 5/0003; G01J 5/0022; C23C 2/06; C23C 2/28; C21D 11/00
USPC ................................................. 148/508, 511
See application file for complete search history.

(56) References Cited

U.S. PATENT DOCUMENTS 3,058,840 A * 10/1962 Kerr .................... C21D 9/60
  118/419
3,307,968 A * 3/1967 Schnedler .............. C23C 2/06
  118/620
(Continued)

FOREIGN PATENT DOCUMENTS

JP  57-185966   11/1982
JP  04-218654   8/1992
(Continued)

OTHER PUBLICATIONS

International Search Report dated Nov. 15, 2011 issued in corresponding PCT Application No. PCT/JP2011/069323 [With English Translation].

*Primary Examiner* — Michael A Lyons
*Assistant Examiner* — Tran M Tran
(74) *Attorney, Agent, or Firm* — Birch, Stewart, Kolasch & Birch, LLP

(57) ABSTRACT

[Object] To determine an alloyed position more precisely even in processes in which induction heating is used in a previous section of alloying, which have been becoming more common in recent years, and a steel sheet is alloyed by being gradually cooled in a heat holding zone.
[Solution] An alloyed position determining method includes a step for acquiring information regarding a result of measurement of radiance from each of a plurality of radiation thermometers installed in a vicinity of a heat holding zone in a hot dip galvanizing line of a steel sheet and along a conveying direction of the steel sheet in the heat holding zone, the radiation thermometers measuring radiance of the steel sheet conveyed, a step for estimating steel sheet temperatures at installation positions of the radiation thermometers by use of information regarding a temperature decreasing pattern of the steel sheet, accompanied by a position change in the conveying direction in the heat holding zone, and information regarding the installation positions of the radiation thermometers, a step for calculating emissivity at the installation positions of the radiation thermometers by use of the estimated steel sheet temperatures at the installation positions of the radiation thermometers and the information regarding the result of measurement of radiance, and a step for determining an alloyed position based on the calculated emissivity.

13 Claims, 15 Drawing Sheets

(51) Int. Cl.
*C23C 2/06* (2006.01)
*C23C 2/28* (2006.01)

(56) References Cited

U.S. PATENT DOCUMENTS

| | | | | |
|---|---|---|---|---|
| 4,243,441 A | * | 1/1981 | Wilson | C21D 9/56 148/508 |
| 4,440,583 A | * | 4/1984 | Ikegami | C21D 11/005 148/500 |
| 4,746,224 A | * | 5/1988 | Mizuno | G01J 5/0022 250/359.1 |
| 4,964,289 A | * | 10/1990 | Dean | B21B 37/32 374/121 |
| 5,052,661 A | * | 10/1991 | Dunlay | C21D 11/00 148/511 |
| 5,156,683 A | * | 10/1992 | Ross | C23C 2/28 118/429 |
| 5,423,926 A | * | 6/1995 | Sashihara | C23C 2/28 148/508 |
| 5,688,051 A | * | 11/1997 | King | G01J 5/0022 374/126 |
| 5,785,772 A | * | 7/1998 | Deka | C21D 9/60 148/508 |
| 6,206,986 B1 | * | 3/2001 | Brisberger | C23C 2/28 148/508 |
| 8,500,927 B2 | * | 8/2013 | Tachibana | B21B 37/76 148/511 |
| 8,529,711 B2 | * | 9/2013 | Fujita | C21D 1/10 148/500 |
| 8,536,514 B2 | * | 9/2013 | Beynon | G01J 5/0022 164/154.6 |
| 8,926,770 B2 | * | 1/2015 | Kobayashi | C23C 2/28 148/508 |
| 2015/0226610 A1 | * | 8/2015 | Uematsu | G01J 5/06 250/338.3 |

FOREIGN PATENT DOCUMENTS

| | | |
|---|---|---|
| JP | 04-370722 | 12/1992 |
| JP | 05-098409 | 4/1993 |
| JP | 05-320852 | 12/1993 |
| JP | 07-011413 | 1/1995 |
| JP | 07-150328 | 6/1995 |
| JP | 11-269627 | 10/1999 |
| JP | 2004-137511 | 5/2004 |
| JP | 2005-163057 | 6/2005 |

* cited by examiner

ALLOYED POSITION DETERMINING METHOD, ALLOYED POSITION DETERMINING APPARATUS, AND RECORDING MEDIUM

TECHNICAL FIELD

This application is a national stage application of International Application No. PCT/JP2011/069323, filed Aug. 26, 2011, the content of which is incorporated by reference in its entirety.

The present invention relates to an alloyed position determining method, an alloyed position determining apparatus, and a recording medium.

BACKGROUND ART

In a hot dip galvanizing line, which is a line for plating a steel sheet with zinc, the steel sheet is conveyed through a molten zinc bath and then heated, so that an alloying layer of zinc and iron is formed on an outer layer of the steel sheet. At this time, it is important in terms of quality management to perform operation so that zinc plating can be alloyed in a predetermined state. That is, both an unalloyed layer in which alloying is insufficient and an overalloyed layer in which alloying is performed too much degrade quality.

Accordingly, for example, the following Patent Document 1 discloses a method to measure radiant energy by se of radiation thermometers at a plurality of points in the height direction of an alloying furnace, to specify an alloyed position by use of the obtained results of measurement of radiant energy, and to control a furnace temperature in the alloying furnace for performing alloying.

Further, the following Patent Document 2 discloses a method to install three or more radiation thermometers in an alloying furnace, and to determine an alloyed position by focusing on differences between adjacent indicated temperatures.

Furthermore, the following Patent Document 3 discloses a method to measure steel sheet radiant temperatures at a plurality of positions in a sheet temperature holding zone in an alloying furnace, and to determine an alloyed position based on emissivity calculated by use of the measurement results.

PRIOR ART DOCUMENT(S)

Patent Document(s)

[Patent Document 1] JPS57-185966A
[Patent Document 2] JPH4-218654A
[Patent Document 3] JPH7-150328A

SUMMARY OF THE INVENTION

Problems to be Solved by the Invention

Techniques disclosed in the above Patent Documents 1 to 3, however, have been made for processes in which flame is lit inside an alloying furnace and a steel sheet is heated to be alloyed. In such furnaces including a high-temperature heat source, stray radiation noise might be a problem and it might be difficult to measure the emissivity precisely. Here, stray radiation noise refers to the phenomenon that, when a heat source exists around a target to be measured, emission from the heat source is mixed into a value measured by a radiation thermometer as disturbance. Mixing of such stray radiation noise can cause a problem that true heat emission from the target to be measured becomes obscure.

Further, in alloying processes in which induction heating is used in a previous section of alloying, which have been becoming more common in recent years, unlike in conventional processes, burning is not performed in a heat holding zone, and a steel sheet is alloyed by being gradually cooled in the heat holding zone. The present inventors have studied such alloying processes and have revealed that the temperature of the steel sheet is decreased in the heat holding zone unlike in conventional processes, as described below.

The techniques disclosed in the above Patent Documents 1 to 3 are each used under a situation in which the heat source exists inside the alloying furnace and the temperature of the steel sheet is maintained almost constantly, so that a decrease in steel sheet temperature is not considered. Therefore, when such a method is applied to the processes that have been becoming more common in recent years, there arises a problem of failure to determine the alloyed position precisely.

Thus, the present invention has been made in view of the above problem, and aims to provide an alloyed position determining method, an alloyed position determining apparatus, and a recording medium each of which enables more precise determination of the alloyed position even in the processes in which induction heating is used in a previous section of alloying, which have been becoming more common in recent years, and the steel sheet is alloyed by being gradually cooled in the heat holding zone.

Means for Solving the Problems

In order to solve the above-described problems, according to an aspect of the present invention, there is provided an alloyed position determining method including a radiance information acquiring step, a steel sheet temperature estimating step, an emissivity calculating step, and an alloyed position determining step. The radiance information acquiring step is for acquiring information regarding a result of measurement of radiance from each of a plurality of radiation thermometers installed in a vicinity of a heat holding zone in a hot dip galvanizing line of a steel sheet and along a conveying direction of the steel sheet in the heat holding zone, the radiation thermometers measuring radiance of the steel sheet conveyed. The steel sheet temperature estimating step is for estimating steel sheet temperatures at installation positions of the radiation thermometers by use of information regarding a temperature decreasing pattern of the steel sheet, accompanied by a position change in the conveying direction in the heat holding zone, and information regarding the installation positions of the radiation thermometers. The emissivity calculating step is for calculating emissivity at the installation positions of the radiation thermometers by use of the estimated steel sheet temperatures estimated at the installation positions of the radiation thermometers and the information regarding the result of measurement of radiance. The alloyed position determining step is for determining an alloyed position based on the calculated emissivity.

In the steel sheet temperature estimating step, an amount of temperature decrease in the steel sheet is preferably calculated based on the information regarding the temperature decreasing pattern of the steel sheet and the information regarding the installation positions of the radiation thermometers, and the estimated steel sheet temperatures are preferably calculated by subtracting the calculated amount of temperature decrease from a temperature of the steel sheet on an entry section of the heat holding zone.

In the steel sheet temperature estimating step, the temperature decreasing pattern may be calculated based on a measured temperature of the steel sheet before the steel sheet enters the heat holding zone, measured with a spectral radiation thermometer, and a measured temperature of the steel sheet in the heat holding zone, measured with a multicolor radiation thermometer, and the steel sheet temperature may be estimated by use of the calculated temperature decreasing pattern and the information regarding the installation positions of the radiation thermometers.

In the alloyed position determining step, when emissivity which is calculated in the emissivity calculating step and which corresponds to a position of an (n−1)(n≥2)-th radiation thermometer from the entry section of the heat holding zone is lower than a predetermined threshold value and emissivity which corresponds to a position of an n-th radiation thermometer is higher than or equal to the predetermined threshold value, it may be determined that a position where alloying has occurred is a section between an installation position of an (n−1)-th radiation thermometer and an installation position of the n-th radiation thermometer in the heat holding zone.

Further, in order to solve the above-described problems, according to another aspect of the present invention, there is provided an alloyed position determining apparatus including a radiance information acquiring unit, a steel sheet temperature estimating unit, an emissivity calculating unit, and an alloyed position determining unit. The radiance information acquiring unit is configured to acquire information regarding a result of measurement of radiance from each of a plurality of radiation thermometers installed in a vicinity of a heat holding zone in a hot dip galvanizing line of a steel sheet and along a conveying direction of the steel sheet in the heat holding zone, the radiation thermometers measuring radiance of the steel sheet conveyed. The steel sheet temperature estimating unit is configured to estimate steel sheet temperatures at installation positions of the radiation thermometers by use of information regarding a temperature decreasing pattern of the steel sheet, accompanied by a position change in the conveying direction in the heat holding zone, and information regarding the installation positions of the radiation thermometers. The emissivity calculating unit is configured to calculate emissivity at the installation positions of the radiation thermometers by use of the estimated steel sheet temperatures estimated at the installation positions of the radiation thermometers, estimated by the steel sheet temperature estimating unit, and the information regarding the result of measurement of radiance. The alloyed position determining unit is configured to determine an alloyed position based on the emissivity calculated by the emissivity calculating unit.

The steel sheet temperature estimating unit preferably calculates an amount of temperature decrease in the steel sheet based on the information regarding the temperature decreasing pattern of the steel sheet and the information regarding the installation positions of the radiation thermometers, and preferably calculates the estimated steel sheet temperatures by subtracting the calculated amount of temperature decrease from a temperature of the steel sheet on an entry section of the heat holding zone.

The steel sheet temperature estimating unit may calculate the temperature decreasing pattern based on a measured temperature of the steel sheet before the steel sheet enters the heat holding zone, measured with a spectral radiation thermometer, and a measured temperature of the steel sheet in the heat holding zone, measured with a multicolor radiation thermometer, and may estimate the steel sheet temperature by use of the calculated temperature decreasing pattern and the information regarding the installation positions of the radiation thermometers.

The alloyed position determining unit may determine, when emissivity which is calculated by the emissivity calculating unit and which corresponds to a position of an (n−1)(n≥2)-th radiation thermometer from the entry section of the heat holding zone is lower than a predetermined threshold value and emissivity which corresponds to a position of an n-th radiation thermometer is higher than or equal to the predetermined threshold value, that a position where alloying has occurred is a section between an installation position of an (n−1)-th radiation thermometer and an installation position of the n-th radiation thermometer the heat holding zone.

Furthermore, in order to solve the above-described problems, according to another aspect of the present invention, there is provided a program for causing a computer to execute a radiance information acquiring function, a steel sheet temperature estimating function, an emissivity calculating function, and an alloyed position determining function. The radiance information acquiring function is to acquire information regarding a result of measurement of radiance from each of a plurality of radiation thermometers installed in a vicinity of a heat holding zone in a hot dip galvanizing line of a steel sheet and along a conveying direction of the steel sheet the heat holding zone, the radiation thermometers measuring radiance of the steel sheet conveyed. The steel sheet temperature estimating function is to estimate steel sheet temperatures at installation positions of the radiation thermometers by use of information regarding a temperature decreasing pattern of the steel sheet, accompanied by a position change in the conveying direction in the heat holding zone, and information regarding the installation positions of the radiation thermometers. The emissivity calculating function is to calculate emissivity at the installation positions of the radiation thermometers by use of the estimated steel sheet temperatures estimated at the installation positions of the radiation thermometers, estimated by the steel sheet temperature estimating function, and the information regarding the result of measurement of radiance. The alloyed position determining function is to determine an alloyed position based on the emissivity calculated by the emissivity calculating function.

Furthermore, in order to solve the above-described problems, according to another aspect of the present invention, there is provided a recording medium having a program recorded thereon for causing a computer to execute a radiance information acquiring function, a steel sheet temperature estimating function, an emissivity calculating function, and an alloyed position determining function. The radiance information acquiring function is to acquire information regarding a result of measurement of radiance from each of a plurality of radiation thermometers installed in a vicinity of a heat holding zone in a hot dip galvanizing line of a steel sheet and along a conveying direction of the steel sheet in the heat holding zone, the radiation thermometers measuring radiance of the steel sheet conveyed. The steel sheet temperature estimating function is to estimate steel sheet temperatures at installation positions of the radiation thermometers by use of information regarding a temperature decreasing pattern of the steel sheet, accompanied by a position change in the conveying direction in the heat holding zone, and information regarding the installation positions of the radiation thermometers. The emissivity calculating function is to calculate emissivity at the installation positions of the radiation thermometers by use of the estimated steel sheet temperatures estimated at the installation positions of the radiation thermometers, estimated by the steel sheet temperature estimating function, and the information regarding the result of measurement of radiance. The alloyed position determining function is to determine an alloyed position based on the emissivity calculated by the emissivity calculating function.

Effects of the Invention

As described above, according to the present invention, calculation of the emissivity considering the decrease in steel sheet temperature in the heat holding zone enables precise estimation of the steel sheet temperature and more precise determination of an alloyed position.

MODE FOR CARRYING OUT THE INVENTION

Figure 1:
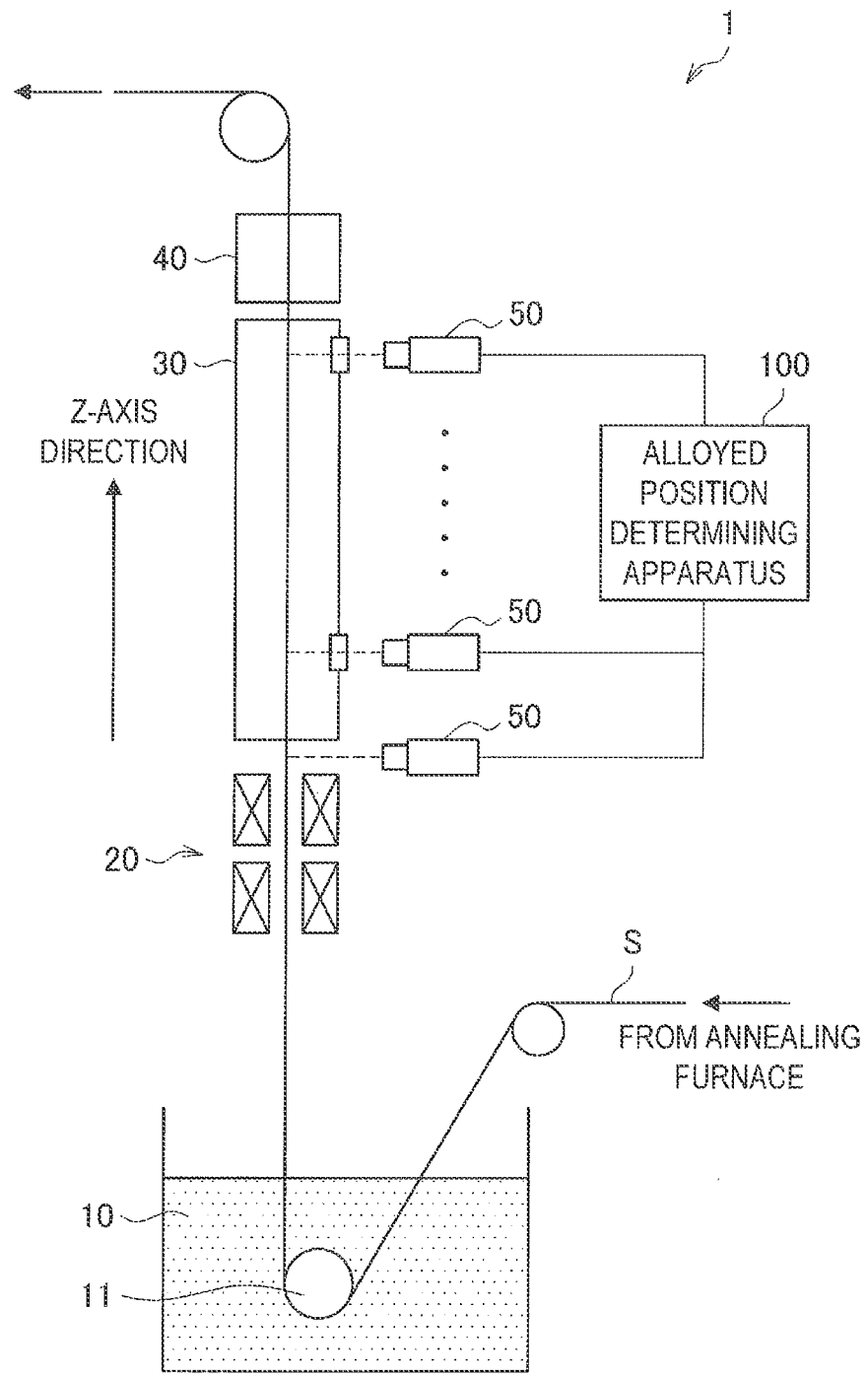
FIG. 1 is an explanatory view schematically showing a hot dip galvanizing line according to a first embodiment of the present invention.

Hereinafter, referring to the appended drawings, preferred embodiments of the present invention will be described in detail. It should be noted that, in this specification and the appended drawings, structural elements that have substantially the same function and structure are denoted with the same reference numerals, and repeated explanation thereof is omitted.

(First Embodiment)
<Regarding Hot Dip Galvanizing Line>

Figure 2:
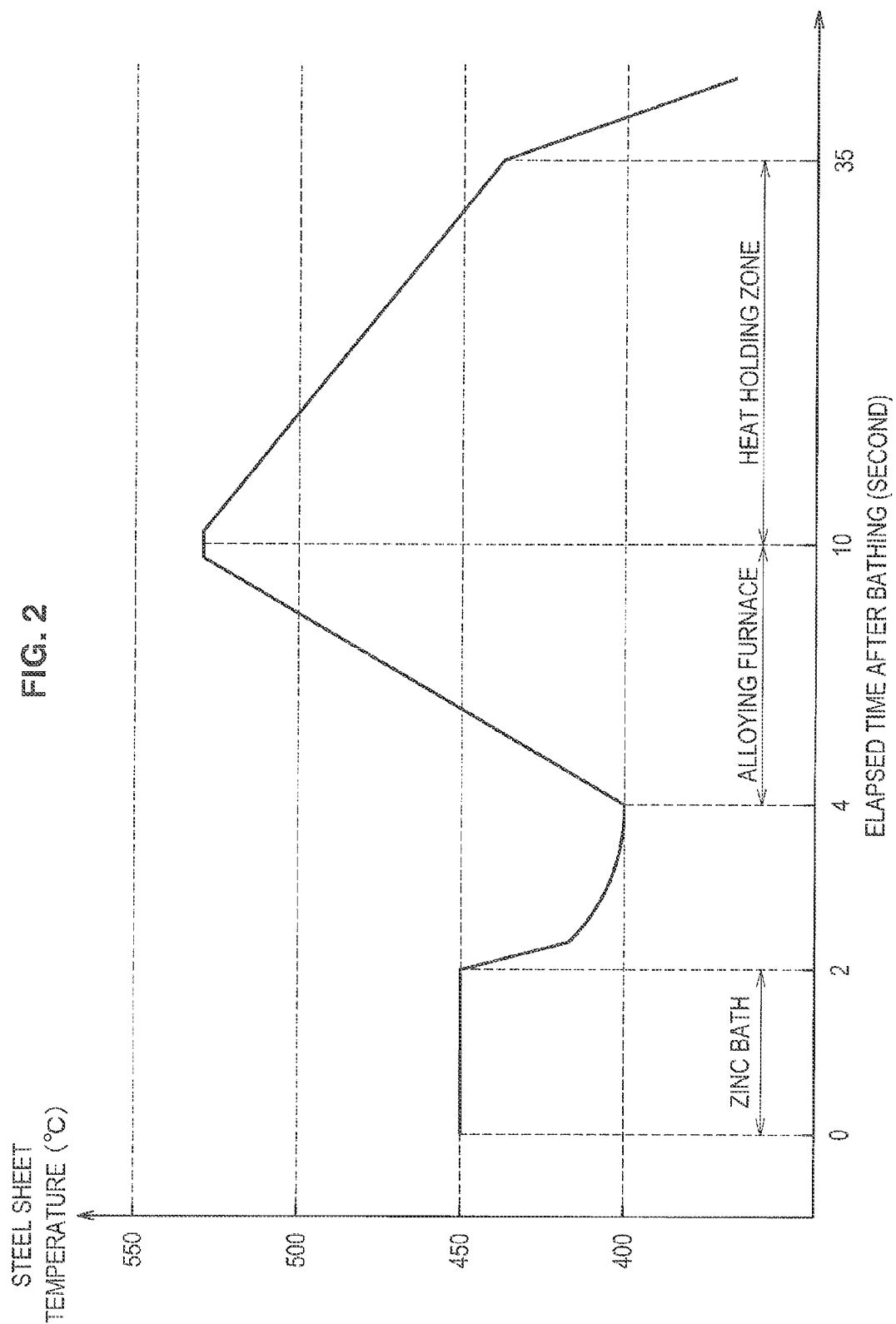
FIG. 2 is a graph showing an example of change in steel sheet temperature in a hot dip galvanizing line.

First, a summary of a hot dip galvanizing line according to a first embodiment of the present invention will be described with reference to FIGS. 1 and 2. FIG. 1 is an explanatory view schematically showing the hot dip galvanizing line according to this embodiment. FIG. 2 is a graph showing an example of change in steel sheet temperature in the hot dip galvanizing line.

First, a hot dip galvanizing line 1 according to this embodiment will be described with reference to FIG. 1.

As shown in FIG. 1, a steel sheet S conveyed from an annealing furnace is immersed in a zinc bath 10 containing molten zinc and a variety of additives. The direction of the steel sheet S is changed by a sink roll (a roll that exists in a molten zinc bath and changes the conveying direction of the steel sheet) 11 installed in the zinc bath 10, and the steel sheet 10 is conveyed in a substantially vertical direction.

The steel sheet S that has exited the zinc bath 10 has hot dip galvanized layers formed on surfaces thereof. The steel sheet S having the galvannealed layers formed on surfaces thereof is conveyed to an alloying furnace 20 such as an induction heater, and is heated to a predetermined steel sheet temperature. The steel sheet S that has exited the alloying furnace 20 (the steel plate S having the galvannealed layers formed on surfaces thereof) is then conveyed to a heat holding zone 30.

The steel sheet S having the galvannealed layers formed on surfaces thereof undergoes alloying of the galvannealed layers at a certain position in the heat holding zone 30. The steel sheet S that has exited the heat holding zone 30 is cooled in a cooling zone 40 and is cooled to almost room temperature.

Here, in the hot dip galvanizing line 1 according to this embodiment, in order to determine the alloyed position of the steel sheet S having the galvannealed layers formed thereon, radiation thermometers 50 are installed at a plurality of positions in the heat holding zone 30 including an entry section of the heat holding zone 30.

Further, the hot dip galvanizing line 1 according to this embodiment includes an alloyed position determining apparatus 100 that determines the alloyed position by use of the measurement results obtained by the radiation thermometers 50.

Here, the state of temperature change in the hot dip galvanizing line 1 according to this embodiment will be described with reference to FIG. 2. Here, in the graph shown in FIG. 2, the vertical axis represents steel sheet temperature and the horizontal axis represents elapsed time after bathing in the zinc bath 10. FIG. 2 shows an example of change in temperature of the steel sheet S being conveyed at a certain sheet-conveying speed.

As shown in FIG. 2, the zinc bath 10 is controlled at a substantially constant temperature (approximately 450° C. in FIG. 2), and in the zinc bath 10, the temperature of the steel sheet S becomes substantially equal to the temperature of the zinc bath 10. Although the temperature of the steel sheet S that has exited the zinc bath 10 is decreased before the steel sheet S enters the alloying furnace 20, when the steel sheet S is conveyed into the alloying furnace 20 using an induction heater or the like, the steel sheet temperature rises. Accordingly, as shown in FIG. 2, at a time when the steel sheet S exits the alloying furnace 20 and enters the heat holding zone 30, the steel sheet temperature is increased to approximately 520° C.

Here, the present inventors' studies have revealed that, in a hot dip galvanizing process that has been becoming more common in recent years, the steel sheet temperature is not constant in the heat holding zone 30, and as shown in FIG. 2, the steel sheet temperature is gradually decreased. The steel sheet having the galvannealed layers formed on surfaces thereof undergoes alloying at a certain position in the heat holding zone 30 while the temperature is gradually decreased in the heat holding zone 30. The plated steel sheet that has undergone alloying exits the heat holding zone 30 and is then conveyed into the cooling zone 40 so as to be further cooled to almost room temperature.

<Regarding Change in Emissivity Accompanied by Progress of Alloying>

Figure 3:
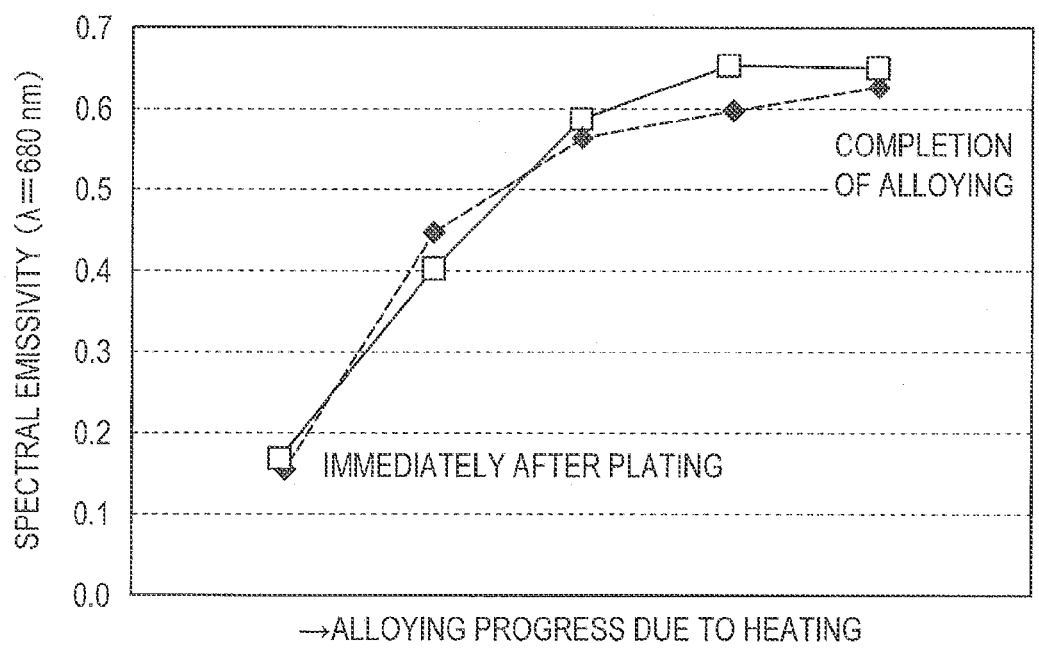
FIG. 3 is a graph showing an example of change in spectral emissivity accompanied by progress of alloying.

Next, change in spectral emissivity (hereinafter also simply referred to as "emissivity") accompanied by progress of alloying will be described with reference to FIG. 3. FIG. 3 is a graph showing an example of the change in spectral emissivity accompanied by the progress of alloying.

It is known that the emissivity (or reflectance) is suddenly changed when zinc on the plated surface is alloyed with a base metal. The steel sheet surface immediately after plating is like a mirror surface and has low emissivity. However, in a process where alloying causes iron to diffuse into a zinc layer, surface roughness of the steel sheet is suddenly increased, and accordingly, the emissivity is increased. For example, it is known that, although the emissivity immediately after plating is approximately 0.2, alloying increases the emissivity to 0.6 to 0.8 depending on the kind of steel.

The present inventors have confirmed such change in emissivity accompanied by the progress of alloying by conducting tests at laboratories. In these tests, a sample made of a steel material was irradiated with a laser and laser intensity reflected by the steel material sample was measured very precisely by use of an integrating sphere. That is, these tests were conducted to measure the reflectance very precisely with cold work. After that, the emissivity was calculated based on the optical law that "emissivity= 1−reflectance". Here, a semiconductor laser with a wavelength of 680 nm was used as a laser source. This laser wavelength corresponds to the wavelength at which emissivity is observed.

In the tests, two steel types of samples were prepared and a plurality of samples were fabricated by changing states of alloying progress depending on heat time for each steel type. The obtained measurement results are shown in FIG. 3. White squares and black rhombuses in FIG. 3 correspond to the respective samples. As shown in FIG. 3, it was confirmed that the emissivity of a sample immediately after plating was approximately 0.17 but that after completion of alloying was approximately 0.6. The initial emissivity of 0.17 is assumed to be a value peculiar to zinc and to be constant at all times. Therefore, as is clear from FIG. 3, it is possible to determine that alloying of the galvannealed layer is completed when the measured emissivity exceeds a predetermined threshold value. Note that the phenomenon that alloying increases the emissivity is caused by increase in surface roughness at a time of alloying. Accordingly, it is considered that similar change in emissivity can occur in a wavelength region from the visible light region to the near infrared light region also when the wavelength is not 680 nm, which is the value at these tests.

<Regarding Configuration of Alloyed Position Determining Apparatus>

Figure 4:
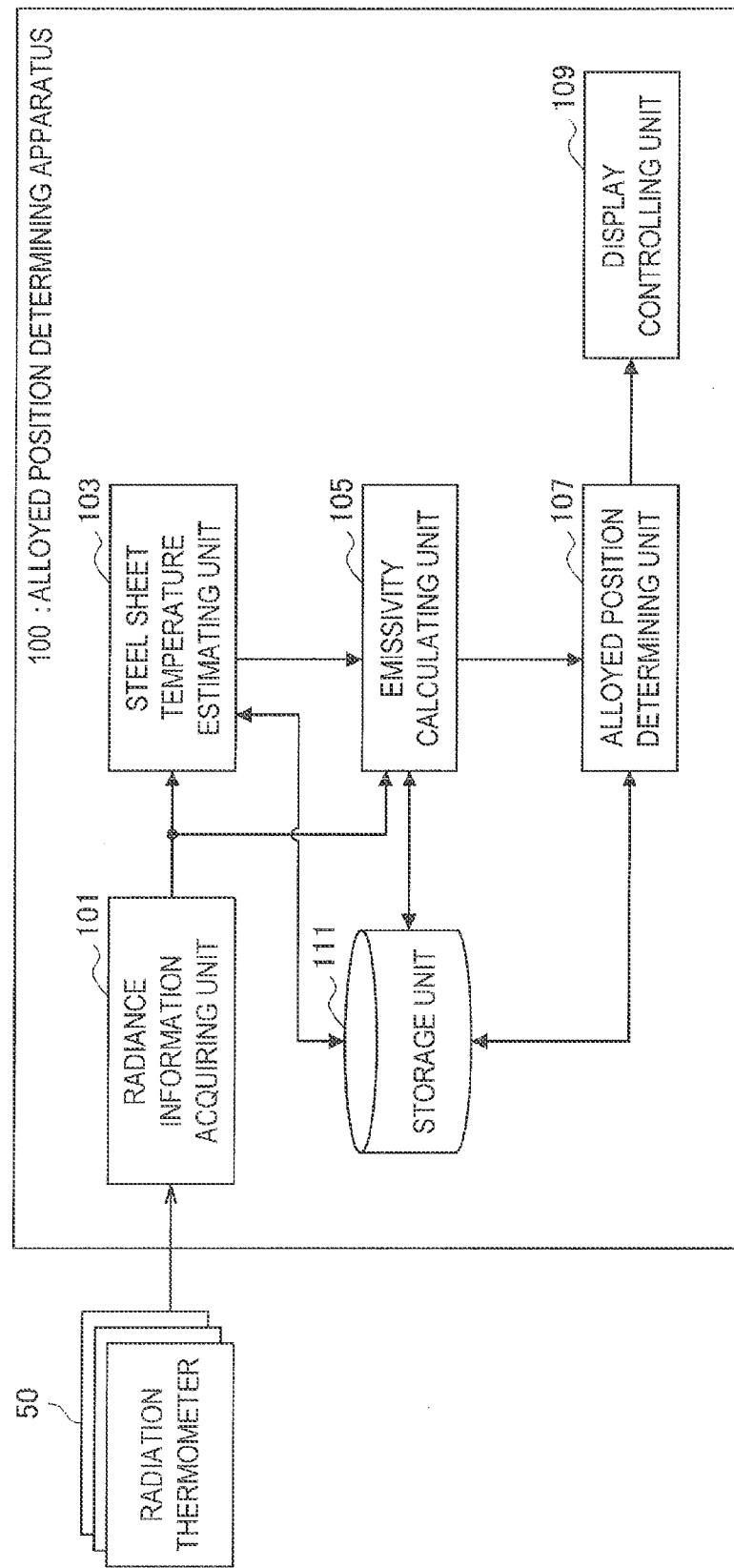
FIG. 4 is a block diagram showing a configuration of an alloyed position determining apparatus according to the embodiment.

Subsequently, a configuration of the alloyed position determining apparatus 100 according to this embodiment will be shown in detail with reference to FIG. 4. FIG. 4 is a block diagram showing the configuration of the alloyed position determining apparatus according to this embodiment.

The alloyed position determining apparatus 100 according to this embodiment mainly includes, as illustrated in FIG. 4, a radiance information acquiring unit 101, a steel sheet temperature estimating unit 103, an emissivity calculating unit 105, an alloyed position determining 107, a display controlling unit 109, and a storage unit 111.

The radiance information acquiring unit 101 is achieved with, for example, a CPU (Central Processing Unit), ROM (Read Only Memory), RAM (Random Access Memory), a communication device, or the like. The radiance information acquiring unit 101 is installed in the vicinity of the heat holding zone 30 in the hot dip galvanizing line 1 and acquires information regarding the results of measurement of radiance (hereinafter referred to as "radiance information") from each of the plurality of radiation thermometers 50 that measure the radiance of the steel sheet S being conveyed.

Figure 5:
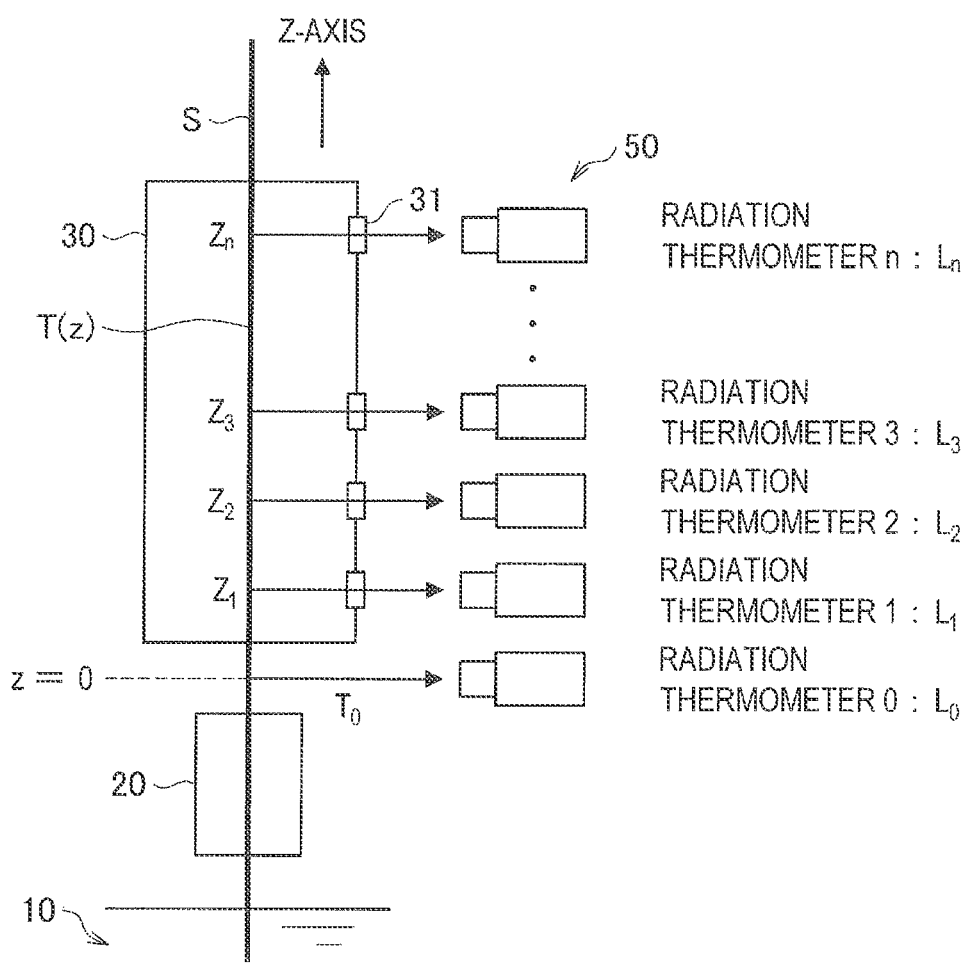
FIG. 5 is an explanatory view showing an example of installation positions of radiation thermometers.

Here, in the hot dip galvanizing line 1 according to this embodiment, as shown in FIG. 5, the plurality of radiation thermometers 50 are installed along the heat holding zone 30. FIG. 5 is an explanatory view showing an example of installation positions of the radiation thermometers. In the following description, it is assumed that n radiation thermometers 50 including a radiation thermometer 1 to a radiation thermometer n are installed in the vicinity of the heat holding zone 30 in addition to a radiation thermometer 0 on the entry section of the heat holding zone 30, as shown in FIG. 5. Note that the radiation thermometers from the radiation thermometer 1 to the radiation thermometer n are each used as a "radiance measuring apparatus". Therefore, the radiation thermometers are set so as to directly output the observed radiance value without performing processing to convert the observed radiance value to a pseudo temperature (black body temperature), which is normally performed inside a radiation thermometer, or temperature information output once as the pseudo temperature is made to be substituted for the Planck's law of black-body radiation to perform processing to convert the temperature information into radiance information.

Note that the vicinity of the heat holding zone 30 refers to an area including the following in the hot dip galvanizing line: the heat holding zone 30; an area between the alloying furnace 20 and the heat holding zone 30; and an area between the heat holding zone 30 and the cooling zone 40 (hereinafter these areas are also collectively referred to as "radiance measuring area").

In the following description, the z-axis is defined along the conveying direction of the steel sheet S and the installation position of the radiation thermometer 0 provided on the entry section of the heat holding zone 30 is set as z=0. Further, the steel sheet temperature immediately before the steel sheet is conveyed into the heat holding zone 30, measured with the radiation thermometer 0, is represented by $T_0$, and the steel sheet temperature in the heat holding zone 30 is represented by $T(z)$. As described above, since it is clear that the steel sheet temperature is gradually decreased in the heat holding zone 30, the steel sheet temperature T(Z) in the heat holding zone 30 is a function of a variable z representing the steel sheet position.

Further, windows 31 are provided at a plurality of positions in the heat holding zone 30 such that the respective radiation thermometers 50 measure heat emission (i.e., radiance) from the steel sheet S through the windows 31 corresponding to the installation positions of the radiation thermometers 50. Here, as shown in FIG. 5, the radiance measured with the n-th radiation thermometer from the entry section of the heat holding zone 30 is represented by $L_n$.

The radiance information acquiring unit 101 according to this embodiment acquires information (radiance information) regarding the radiance $L_n$ measured with each radiation thermometer from each radiation thermometer 50 installed as shown in FIG. 5, and outputs the acquired information to the steel sheet temperature estimating unit 103 and the emissivity calculating unit 105, which will be described later.

Further, the radiance information acquiring unit 101 may associate the radiance information acquired from each radiation thermometer 50 with time information or the like regarding date and time when the radiance information is acquired, and may store the associated information as history information in the storage unit 111, which will be described later.

The steel sheet temperature estimating unit 103 is achieved with, for example, a CPU, ROM, RAM, or the like. The steel sheet temperature estimating unit 103 estimates steel sheet temperatures at predetermined positions in the heat holding zone 30 by use of information regarding a temperature decreasing pattern of the steel sheet accompanied by position change in the conveying direction of the steel sheet in the heat holding zone 30 and information regarding installation positions of the radiation thermometers 50. Here, the information regarding the temperature decreasing pattern of the steel sheet (hereinafter also simply referred to as "steel sheet temperature decreasing pattern") is specified in advance for each manufacturing condition, i.e., the condition of the steel type, the thickness, or the conveying speed of the steel sheet, by use of operation achievement data in the past, and is stored in the storage unit 111. Alternatively, the steel sheet temperature decreasing pattern can care be calculated from the results of heat transfer model simulation regarding extracted heat from the steel sheet due to an atmosphere in the furnace and an inner wall, or the like. In this case, the heat transfer model simulation is calculated in a form of a decrease in temperature with respect to elapsed time of conveying the steel sheet in the heat holding zone 30. Accordingly, in such a case, by combination with information of the conveying speed, the steel sheet temperature decreasing pattern accompanied by the position change in the conveying direction of the steel sheet is calculated. Such a steel sheet temperature decreasing pattern is, for example, stored in the storage unit 111. The steel sheet temperature decreasing pattern may be stored in the storage unit 111 in a form of a database for each type of the steel sheet, or may be stored in the storage unit 111 in a form of a lookup table for each type of the steel sheet.

Figure 6:
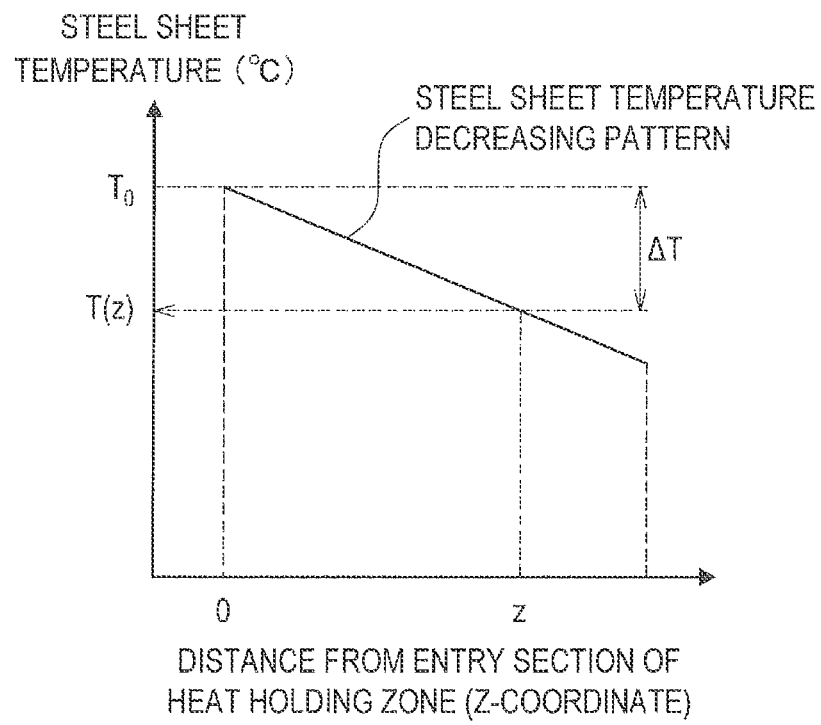
FIG. 6 is an explanatory view showing an estimating method of a steel sheet temperature.

An example of estimating processing of the steel sheet temperature, performed in the steel sheet temperature estimating unit 103, will be specifically described with reference to FIG. 6. FIG. 6 is an explanatory view showing an estimating method of the steel sheet temperature. In the example shown in FIG. 6, as the steel sheet temperature decreasing pattern, the inclination of a straight line representing the degree of decrease in the steel sheet temperature in the heat holding zone 30 is used. Further, this straight line is represented by a straight line in a coordinate system having a horizontal axis representing the distance from the entry section of the heat holding zone (z-coordinate) and a vertical axis representing the steel sheet temperature (° C.). That is, in the example shown in FIG. 6 the distance from the entry section of the heat holding zone corresponds to the installation position of the radiation thermometer.

The steel sheet temperature estimating unit 103 calculates the amount of a decrease in steel sheet temperature based on the steel sheet temperature decreasing pattern stored in the storage unit 111 and the installation positions (z-coordinates) of the radiation thermometers. For example, when the steel sheet temperature decreasing pattern is shown as the inclination representing the degree of decrease in the steel sheet temperature as shown in FIG. 6, the steel sheet temperature estimating unit 103 first calculates the amount of temperature decrease represented by $\Delta T$ in FIG. 6 by use of the distance from the entry section of the heat holding zone. Next, the steel sheet temperature estimating unit 103 subtracts the amount of temperature decrease $\Delta T$ calculated from the steel sheet temperature $T_0$ immediately before the steel sheet is conveyed into the heat holding zone 30, the steel sheet temperature $T_0$ being calculated by use of radiance $L_0$ of the radiation thermometer 0 in FIG. 5. Accordingly, the steel sheet temperature estimating unit 103 can calculate the estimated steel sheet temperature T(z) at the position z in the heat holding zone. That is, the estimated steel sheet temperature is the amount represented by $T(z) = T_0 - \Delta T$. Note that the temperature $T_0$ is obtained by converting the observed radiance $L_0$ into temperature on the assumption that the emissivity is 0.2 (more precisely, the emissivity may be 0.17) because alloying is not started at this position.

By the above-described method, the steel sheet temperature estimating unit 103 calculates the estimated steel sheet temperature at each installation position of the radiation thermometer corresponding to the radiance information notified by the radiance information acquiring unit 101. That is, as shown in FIG. 5, when the n radiation thermometers 50 are installed, the steel sheet temperature estimating unit 103 calculates each of the following estimated steel sheet temperatures: an estimated steel sheet temperature $T(z_1)$ corresponding to an installation position $z_1$ of the radiation thermometer 1 to an estimated steel sheet temperature $T(z_n)$ corresponding to an installation position $z_n$ of the radiation thermometer n.

The steel sheet temperature estimating unit 103 outputs each estimated steel sheet temperature $T(z_n)$, calculated in the above manner, to the emissivity calculating unit 105. Further, the steel sheet, temperature estimating unit 103 may associate the calculated estimated steel sheet temperature with time information or the like regarding the date and time when the estimated steel sheet temperature is calculated, and may record the associated information as history information in the storage unit 111, which will be described later.

The emissivity calculating unit 105 is achieved with, for example, a CPU, ROM, RAM, or the like. The emissivity calculating unit 105 calculates emissivity $\epsilon_z$ by use of the estimated steel sheet temperature T(z) at a predetermined position in the heat holding zone, the estimated steel sheet temperature T(z) being estimated by the steel sheet temperature estimating unit 103, and the radiance information $L_n$ at a position corresponding to the estimated steel sheet temperature T(z) acquired by the radiance information acquiring unit 101 (i.e., the radiance $L_z$ at a position z).

Specifically, the emissivity calculating unit 105 calculates the emissivity $\varepsilon_z$ from the following expression 101 by use of the radiance information $L_n$ and the calculated estimated steel sheet temperature $T(z)$.

[Math 1]

$$\varepsilon_z = \frac{L_n}{L_b(T)} = \frac{L_n}{c_1 \lambda^{-5}} \times \left[\exp\left\{\frac{c_2}{\lambda \cdot T(z)}\right\} - 1\right] \quad \text{(Expression 101)}$$

Here, in the above expression 101, $L_b(T)$ represents radiance of the black body at a temperature $T[K]$, a constant $c_1$ is a value represented by use of the speed c of light in vacuum and a Planck's constant h, and a constant $c_2$ is a value represented by use of the speed c of light in vacuum, the Planck's constant h, and a Boltzmann's constant k. Details of these values are shown in the following expressions 102 and 103. Further, $\lambda$ is a wavelength observed by the radiation thermometer 50 and is set in the infrared region (more specifically, near infrared region, such as 1.5 μm).

[Math 2]

$$c_1 = 2c^2 h = 1.1910 \times 10^{-16} [W \cdot m^2] \quad \text{(Expression 102)}$$

$$c_2 = \frac{ch}{k} = 0.014388 [m \cdot K] \quad \text{(Expression 103)}$$

In the following description, prior to detailed explanation of emissivity calculating processing performed by the emissivity calculating unit 105, first, some problems influencing the calculation of the emissivity will be described.

In processes that have been becoming more common in recent years, unlike in conventional processes, there are no conspicuous heat source such as burner flame in the heat holding zone where alloying proceeds. However, even under such circumstances, the inner wall of the heat holding zone 30 having heat can serve as a source of stray radiation noise. Therefore, first, the following description will briefly explain how the calculation of the emissivity is influenced by stray radiation noise from the inner wall of the heat holding zone.

Figure 7:
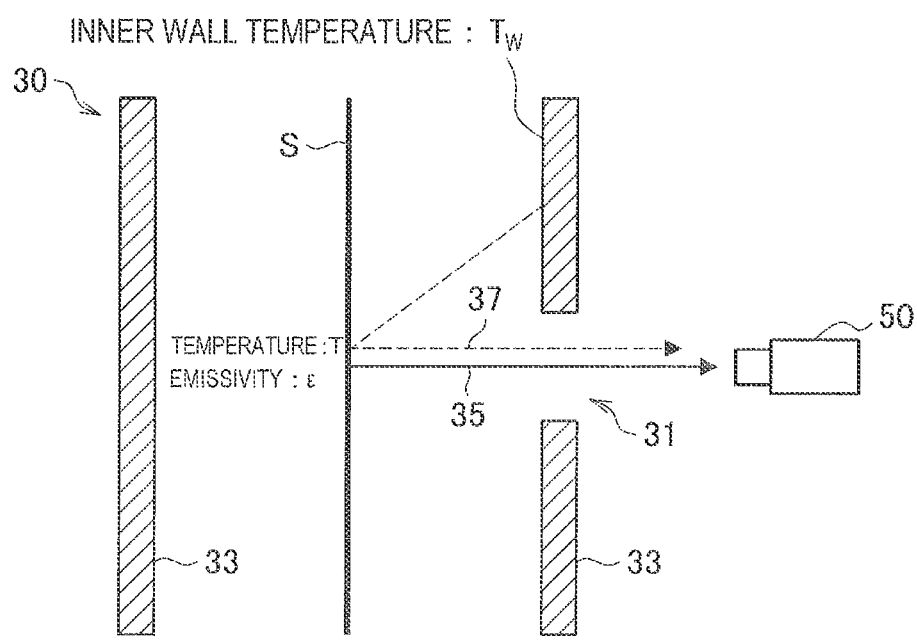
FIG. 7 is an explanatory view for explaining stray radiation noise.

FIG. 7 is an explanatory view for explaining stray radiation noise, and schematically shows the state in the heat holding zone 30. In the heat holding zone 30, the steel sheet S is conveyed, which has the steel sheet temperature T [° C.] and the emissivity $\varepsilon$. Further, an inner wall 33 of the heat holding zone 30 is heated by heat emission or the like from the steel sheet S conveyed at higher temperatures, and the inner wall temperature is assumed to reach Tw [° C.]. The radiation thermometer 50 installed in the vicinity of the heat holding zone 30 measures heat emission from the steel sheet S, i.e., spontaneous light emission 35. Further, since the inner wall 33 of the heat holding zone also has heat, the inner wall 33 of the heat holding zone also emits heat emission. The heat emission is reflected by the steel sheet S and the radiation thermometer 50 observes the reflected heat emission as stray radiation 37 at the same time, in this manner, the radiance $L_z$ observed by the radiation thermometer 50 is the sum of the radiance due to spontaneous light emission from the steel sheet and the radiance due to heat emission from the inner wall, as shown in the following expression 104. The radiance due to heat emission from the inner wall is called stray radiation noise, and serves as an error factor.

[Math 3]

$$L_z = \varepsilon L_b(T) + (1-\varepsilon) \cdot L_b(T_w) \quad \text{(Expression 104)}$$

Here, in the expression 104, $\varepsilon$ represents the true emissivity of the steel sheet and the right side first term represents the radiance due to spontaneous light emission from the steel sheet. Further, the right side second term represents the radiance (stray radiation noise) mixed by reflection by the steel sheet, of heat emission from the inner wall of the heat holding zone.

Here, as is clear from the above expression 104, stray radiation noise is relatively increased when the temperature difference between the target steel sheet and the inner wall is small or when the true emissivity $\varepsilon$ is a small value. Accordingly, the observed radiance $L_z$ deviates from the true heat emission from the steel sheet.

Figure 8:
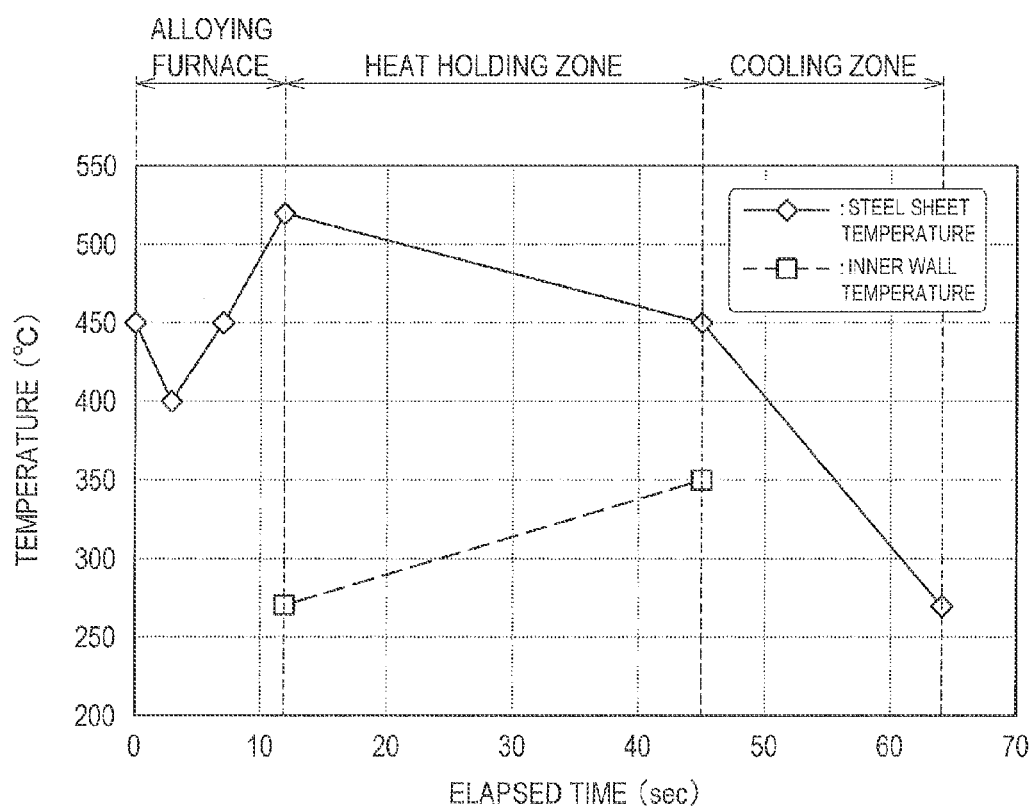
FIG. 8 is a graph showing an example of temperature change in steel sheet temperature and inner wall temperature.

Further, also when the estimated steel sheet temperature deviates from the true value, the calculated emissivity becomes imprecise. The present inventors have investigated whether alloying can be determined based on the emissivity in a state where such disturbance exists. FIG. 8 is a graph showing a relation between the steel sheet temperature and the inner wall temperature at a time when the steel sheet passes through the heat holding zone in the hot dip galvanizing line 1 according to this embodiment. Note that in FIG. 8, the horizontal axis represents elapsed time after the steel sheet exits from the zinc bath 10, instead of the z-axis coordinate.

As is clear from FIG. 8, it is found that the steel sheet S conveyed into the heat holding zone 30 at approximately 520° C. is gradually cooled in the heat holding zone 30. It is also found that the inner wall temperature is gradually increased and near an delivery section of the heat holding zone, the temperature is increased to a temperature that is lower than the steel sheet temperature by approximately 100° C.

The present inventors have assumed that four radiation thermometers are installed at positions where the elapsed time is 12 seconds; 21 seconds, 31 seconds, and 40 seconds (where the steel sheet temperature is 520° C., 500° C., 480° C., and 460° C.), respectively, under a condition of temperature change shown FIG. 8 (i.e., temperature change in a production line). On that assumption, the present inventors have calculated pseudo emissivity from the expression 101 by use of the radiance $L_z$ calculated from the expression 104 and the estimated steel sheet temperature T(z) shown in FIG. 8.

Figure 9A:
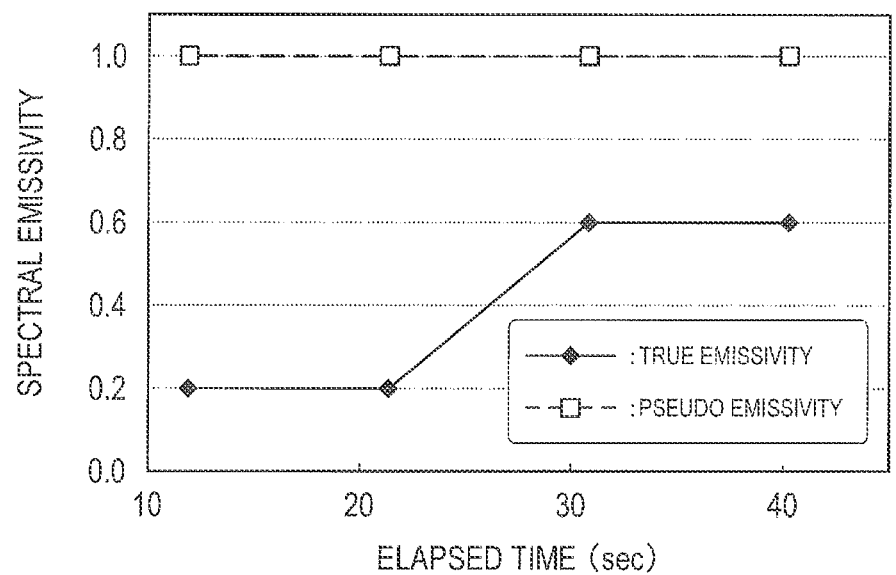
FIG. 9A is a graph showing a relation between true emissivity and pseudo emissivity.
Figure 9B:
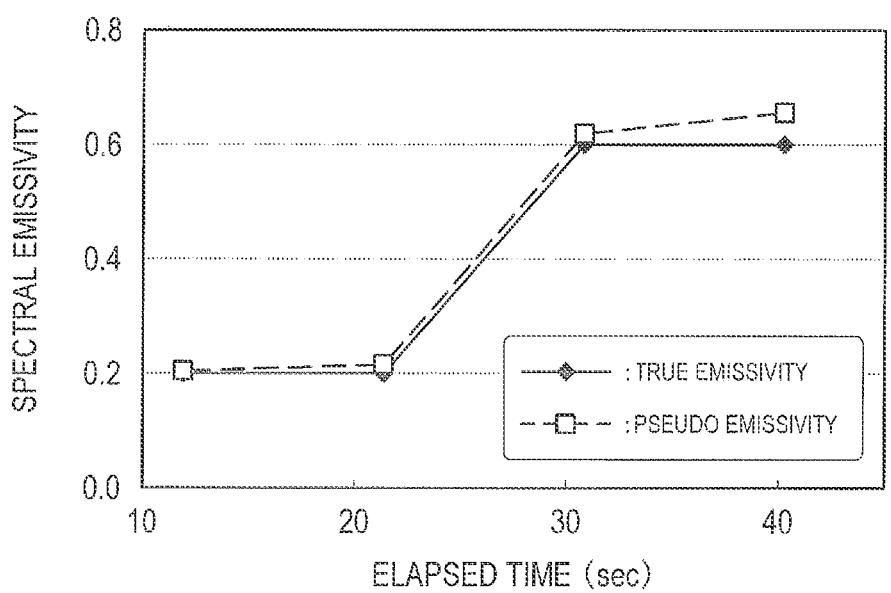
FIG. 9B is a graph showing a relation between true emissivity and pseudo emissivity.

FIGS. 9A and 9B each show the results of calculation of influence of stray radiation noise due to high and low of the inner wall temperature on the assumption that alloying occurs at the center of the heat holding zone. FIGS. 9A and 9B are each a graph showing a relation between the true emissivity and the pseudo emissivity. Here, the values shown in FIG. 8 are each used as the steel sheet temperature.

FIG. 9A shows the calculation results when the steel sheet temperature is equal to the inner wall temperature (that is, $T=T_w$ is satisfied) on the assumption of an alloying furnace employing a gas burner heating method of the conventional art before heating with an induction heater is introduced. The condition that the steel sheet temperature is equal to the inner wall temperature corresponds to setting that temperature change in inner wall temperature is the same as temperature change in steel sheet temperature in the temperature change shown in FIG. 8.

As is clear from the expression 104, as the true emissivity of the steel sheet is low, stray radiation noise contributes more greatly. Therefore, even when the true emissivity is changed in a manner shown in FIG. 9A, the pseudo emissivity is 1. In other words, since the condition that $T=T_w$ is satisfied, the term relating to the emissivity $\epsilon$ in the expression 104 is cancelled, and the obtained radiance $L_z$ becomes equal to the radiance $L_b(T)$ emitted from the black body at the temperature T. Therefore, the pseudo emissivity $\epsilon_z$ calculated from the expression 101 is constantly 1.

In contrast, the example shown in FIG. 9B shows the results when the pseudo emissivity is simulated in accordance with the temperature changing pattern shown in FIG. 8. As is clear from FIG. 9B, the true emissivity of the steel sheet substantially corresponds to the pseudo emissivity. Further, it is found that the pseudo emissivity is slightly higher than the true emissivity at an observing position when the elapsed time is 40 seconds. This is an influence of stray radiation noise. Therefore, it is found that, in processes that have been becoming more common in recent years, the steel sheet temperature in the heat holding zone 30 is higher than the inner wall temperature of the heat holding zone, and that, as is clear from the temperature changing pattern shown in FIG. 8, the influence of stray radiation noise is slight and the change in the emissivity due to alloying can be sufficiently detected.

The influence of stray radiation noise when the emissivity is calculated has been explained above.

Subsequently, the influence of estimation accuracy of the steel sheet temperature when the emissivity is calculated will be briefly explained.

In order that the emissivity calculation unit 105 calculates the emissivity, it is necessary to substitute the estimated steel sheet temperature T for the expression 101. Therefore, in order to discuss the influence of the estimation accuracy of the estimated steel sheet temperature on the calculated emissivity, the preset inventors have calculated the pseudo emissivity when the estimated value of the steel sheet temperature deviates from the true value. Here, when the pseudo emissivity is calculated, the inner wall temperature in the heat holding zone is set as the inner wall temperature with the temperature change shown in FIG. 8.

Figure 10:
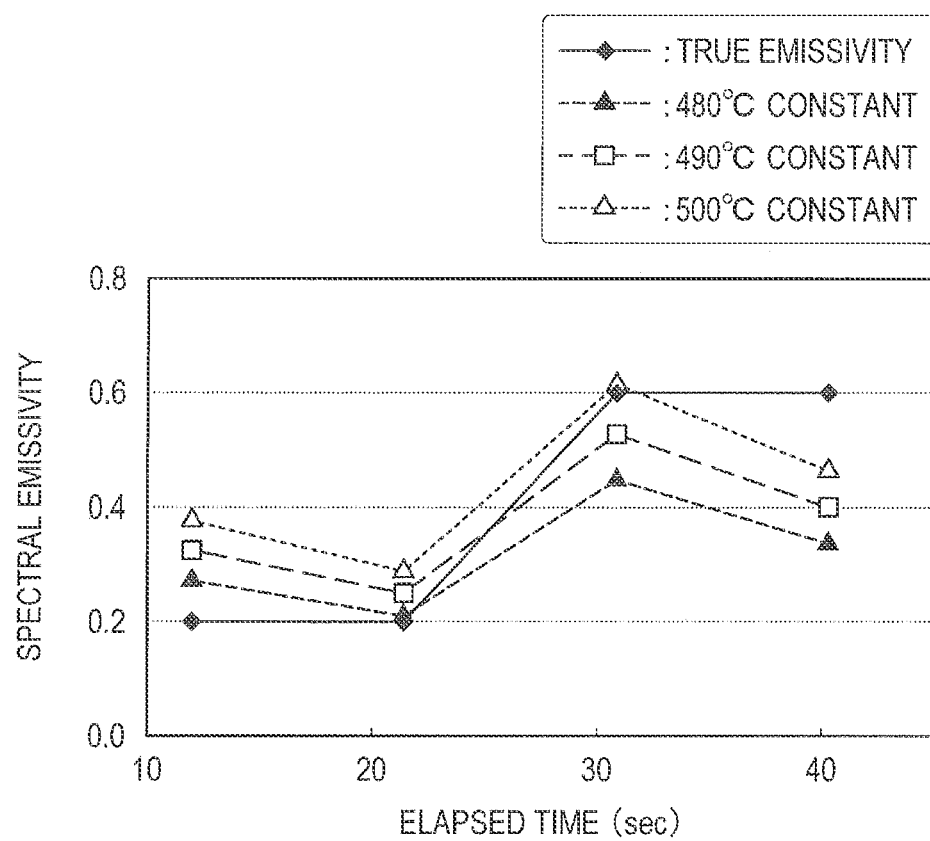
FIG. 10 is a graph showing a relation between spectral emissivity and true emissivity when a steel sheet temperature is assumed to be constant.

The obtained results are shown in FIG. 10. FIG. 10 is a graph showing a relation between the spectral emissivity and the true emissivity when the steel sheet temperature is assumed to be constant, even when the true steel sheet temperature is the values shown in FIG. 8. The calculation results shown in FIG. 10 are obtained under the condition that the steel sheet temperature is not decreased in the heat holding zone and is constant (that is, under the condition assuming the alloying furnace employing the gas burner heating method of the conventional art). According to the calculation results, the calculated emissivity is estimated higher than the true value in a range where the elapsed time is short, and the calculated emissivity is estimated lower than the true value in a range where the elapsed time is long.

As is clear from the results shown in FIG. 10, under the condition where the steel sheet temperature is constant in the heat holding zone 30 (that is, under the condition where the steel sheet temperature decrease is not considered), it is unclear whether the change of the pseudo emissivity is truly caused by the emissivity or the temperature change, and it is difficult to determine an alloyed position by setting a predetermined threshold value in the emissivity.

Accordingly, in view of the above-described knowledge, the emissivity calculation unit 105 according to this embodiment calculates the emissivity $\epsilon_z$ based on the expression 101 by use of the estimated steel sheet temperature T(z) at a predetermined position in the heat holding zone, the estimated steel sheet temperature T(z) being estimated by the steel sheet temperature estimating unit 103, and the radiance information $L_n$ at a position corresponding to the estimated steel sheet temperature T(z) acquired by the radiance information acquiring unit 101 (i.e., the radiance $L_z$ at the position z).

For emissivity calculating processing, the emissivity calculating unit 105 performs processing considering the steel sheet temperature decrease in the heat holding zone 30 by use of the estimated steel sheet temperature obtained by the steel sheet temperature estimating unit 103. Therefore, as described above, the error in calculation of emissivity due to the estimation accuracy of the estimated steel sheet temperature can be suppressed. Further, since the inner wall temperature of the heat holding zone is lower than the steel sheet temperature, the influence of stray radiation noise contained in the calculated emissivity is small.

The emissivity calculating unit 105 according to this embodiment calculates the emissivity $\epsilon_z$ at the respective installation positions of the radiation thermometers 50, and Outputs the calculated emissivity $\epsilon_z$ to the alloyed position determining unit 107, which will be described later. Further, the emissivity calculating unit 105 may associate the calculated emissivity with time information or the like regarding the date and time when the emissivity is calculated, and may record the associated information as history information in the storage unit 111, which will be described later.

Note that the difference between the steel sheet temperature and the inner wall temperature shown in FIG. 8 (at least approximately 100° C.) is only an example, and the temperature difference between the steel sheet temperature and the inner wall temperature is not limited to such a temperature difference and the inner wall temperature may be other temperature as long as the temperature does not serve as disturbance when the emissivity is calculated.

Figure 11:
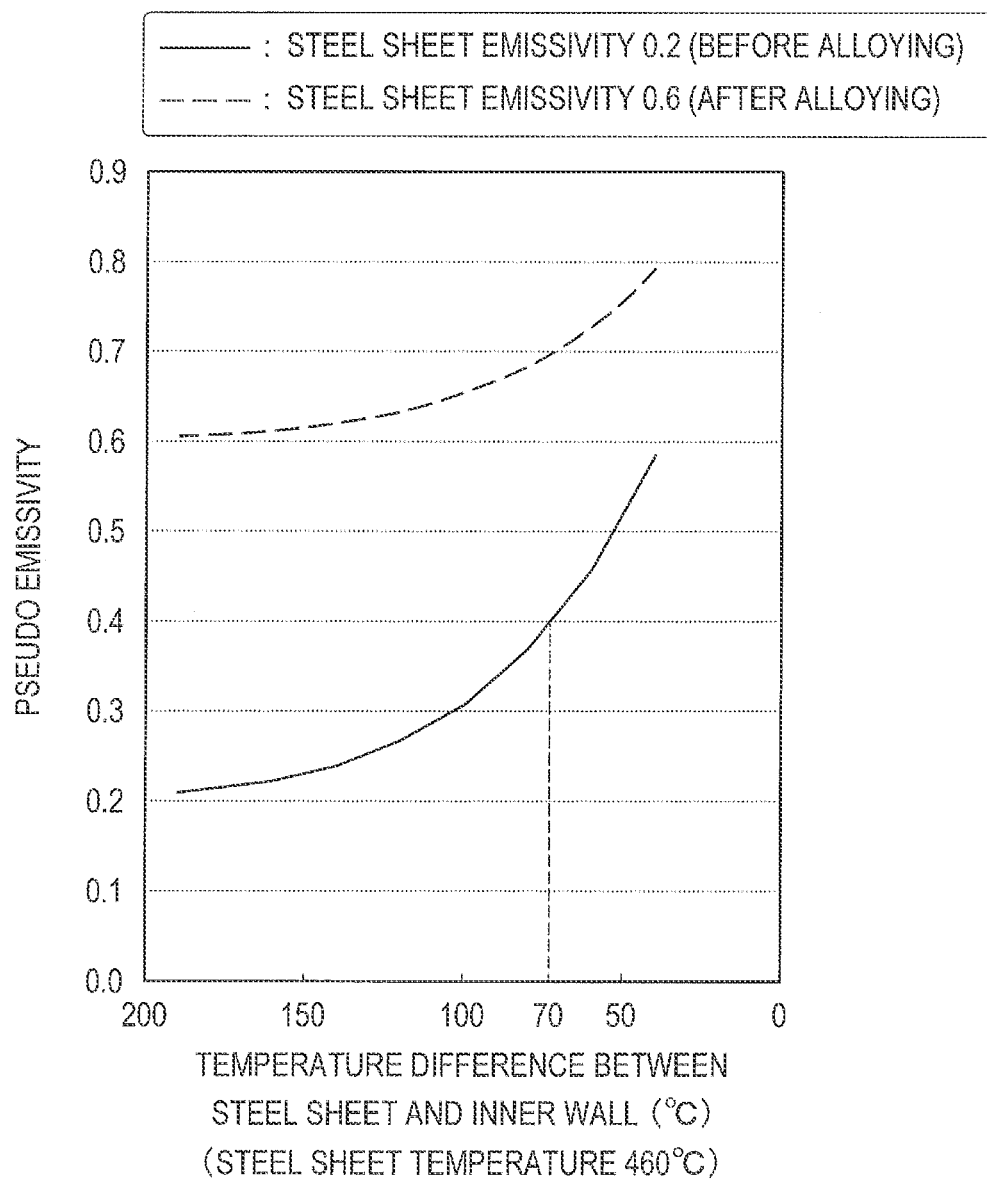
FIG. 11 is a graph showing a relation between a temperature difference between steel sheet temperature and inner wall temperature and pseudo emissivity.

FIG. 11 shows the results of calculation regarding how the pseudo emissivity is changed when the temperature difference between the steel sheet and the inner wall is changed on the assumption that the steel sheet temperature is 460° C. At this time, a solid line represents the change in the emissivity before alloying and is the results when the true emissivity is assumed to be 0.2. Further, a dotted line represents the change in the emissivity after alloying and is the results when the true emissivity is assumed to be 0.6.

When focusing on the emissivity represented by the solid line in FIG. 11, as is clear from the graph, it is found that the influence of stray radiation noise is negligible as long as the temperature difference between the steel sheet and the inner wall is 200° C. or more. Further, when the threshold value for determining, by the alloyed position determining unit 107, which will be described later, whether or not alloying occurs is set to the emissivity of 0.4, when the temperature difference between the steel sheet and the inner wall is 70° C. or less, the pseudo emissivity before alloying is observed as if it is the emissivity after alloying. Therefore, the temperature difference is an acceptable limit value of the inner wall temperature. In a similar manner, when focusing on the graph represented by the dotted line, it is found that the emissivity (precisely 0.6) after alloying is apparently increased by decrease in the temperature difference.

The alloyed position determining unit 107 is achieved with, for example, a CPU, ROM, RAM, or the like. The alloyed position determining unit 107 determines the position where the galvannealed layer is alloyed in the heat holding zone based on the emissivity $\epsilon_z$ calculated by the emissivity calculating unit 105. In order to determine whether or not alloying occurs, a predetermined threshold value is used. As shown in FIG. 3, the emissivity of the steel sheet before alloying is a low value while the emissivity of the steel sheet is changed to a large value by alloying. Accordingly, the alloyed position determining unit 107 can determine whether or not alloying occurs by use of a predetermined threshold value in accordance with the type of the steel sheet and galvannealed layer, or the like. That is, when the calculated emissivity is lower than the predetermined threshold value, the alloyed position determining unit 107 determines that alloying has not occurred yet, and when the calculated emissivity is higher than or equal to the predetermined threshold value, the alloyed position determining unit 107 determines that the alloying has occurred. Such a threshold value can be set as appropriate in accordance with the type of the steel sheet or galvannealed layer, or the like, and for example, the threshold value can be set to approximately 0.3 or 0.4.

More specifically, the alloyed position determining unit 107 determines whether or not all the emissivity $\epsilon_z$ notified by the emissivity calculating unit 107 is higher than or equal to the predetermined threshold value. For example, when the emissivity $\epsilon_z$ corresponding to a position of the (n−1)(n≥2)-th radiation thermometer from the entry section of the heat holding zone is lower than the predetermined threshold value and the emissivity $\epsilon_z$ corresponding to a position of the n-th radiation thermometer is higher than or equal to the predetermined threshold value, the alloyed position determining unit 107 determines that the position where alloying has occurred is a section in the heat hold zone between an installation position of the (n−1)-th radiation thermometer and an installation position of the n-th radiation thermometer.

For example, as shown in FIG. 5, when the n radiation thermometers are installed, the emissivity $\epsilon_{z2}$ corresponding to a position of the radiation thermometer 2 is lower than the predetermined threshold value, and the emissivity $\epsilon_{z3}$ corresponding to a position of the radiation thermometer 3 is higher than or equal to the predetermined threshold value for the first time, the alloyed position determining unit 107 determines that the alloyed position is a section between an installation position of the radiation thermometer 2 and an installation position of the radiation thermometer 3 (i.e., a section between $z_2$ and $z_3$ in FIG. 5).

Note that the alloyed position determining unit 107 has information regarding where each radiation thermometer is installed (i.e., information regarding an installation order and installation positions of the plurality of radiation thermometers).

The alloyed position determining unit 107 determines the position where alloying has occurred, and then outputs the obtained results to the display controlling unit 109, which will be described later. Further, the alloyed position determining unit 107 may associate the determination results regarding the alloyed position with time information or the like regarding the date and time when the determination is performed, and may record the associated information as history information in the storage unit 111, which will be described later.

The display controlling unit 109 is achieved with, for example, a CPU, ROM, RAM, or the like. The display controlling unit 109 controls display when the information regarding the alloyed position transmitted from the alloyed position determining unit 107 is displayed on a display unit of a display or the like included in the alloyed position determining apparatus 100. Further, the display controlling unit 109 can allow the display unit to display a variety of pieces of information such as the calculated estimated steel sheet temperature, the calculated emissivity value, and a graph showing change of these values, in addition to the information regarding the alloyed position. The display controlling unit 109 allows the display unit to display the results regarding the alloyed position, and thereby a user of the alloyed position determining apparatus 100 can acquire the information regarding the alloyed position of the steel sheet S that is being conveyed.

The storage unit 111 is an example of a storage device included in the alloyed position determining apparatus 100. The storage unit 111 stores information regarding the temperature decreasing pattern of the steel sheet that is used when the steel sheet temperature estimating unit 103 estimates the estimated steel sheet temperature. The storage unit 111 may store information regarding the installation order and the installation positions of the plurality of radiation thermometers. Further, the storage unit 111 stores, as appropriate, a variety of parameters, development processes of processing, and the like, which need to be stored when the alloyed position determining apparatus 100 according to this embodiment performs certain processing, or a variety of databases or the like. For the storage unit 111, reading and writing can be freely performed by the radiance information acquiring unit 101, the steel sheet temperature estimating unit 103, the emissivity calculating unit 105, the alloyed position determining unit 107, the display controlling unit 109, and the like.

An example of functions of the alloyed position determining apparatus 100 according to this embodiment is described above. Each of the structural elements described above may be configured using a general-purpose material or circuit, or may be configured from hardware dedicated to the function of each structural element. Further, the functions of each structural element may be all performed by a CPU or the like. Accordingly, the configuration to be used can be changed as appropriate according to the technical level at the time of carrying out this embodiment.

Note that a computer program for realizing each function of the above-described alloyed position determining apparatus according to this embodiment can be produced and incorporated in a personal computer or the like. Further, it is possible to provide a computer-readable recording medium storing such a computer program therein. Examples of the recording medium include a magnetic disk, an optical disk, a magneto-optical disk, flash memory, and the like. Further, the above-described computer program may be distributed via a network, for example, without using the recording medium.

<Flow of Alloyed Position Determining Method>

Figure 12:
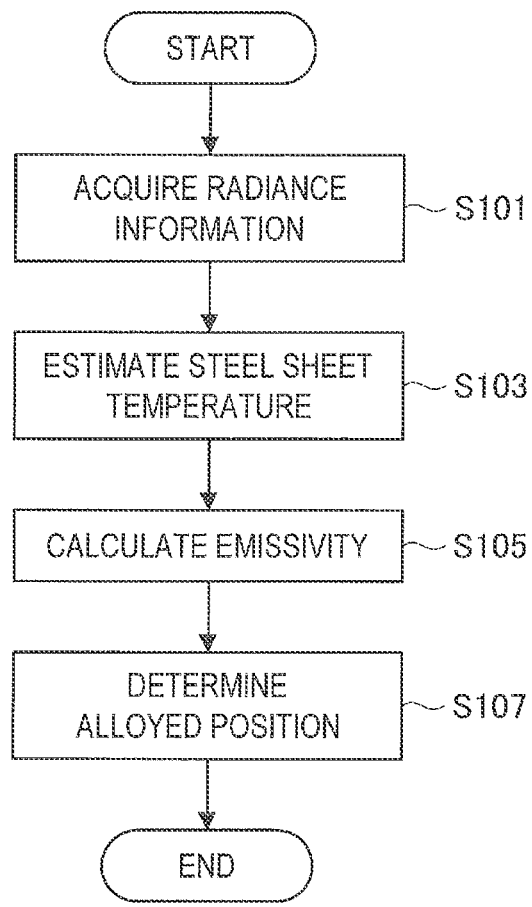
FIG. 12 is a flow chart showing a flow of an alloyed position determining method according to the embodiment.

Next, with reference to FIG. 12, a flow of an alloyed position determining method according to this embodiment will be described. FIG. 12 is a flow chart showing the flow of the alloyed position determining method according to this embodiment.

In the alloyed position determining method according to this embodiment, first, the radiance information acquiring unit 101 acquires information regarding the radiance (radiance information) measured by the plurality of radiation thermometers 50, from the radiation thermometers installed in the vicinity of the hot dip galvanizing line 1 (step S101). The radiance information acquiring unit 101 outputs the acquired radiance information to the steel sheet temperature estimating unit 103 and the emissivity calculating unit 105.

Next, the steel sheet temperature estimating unit 103 estimates the steel sheet temperature T(z) at a predetermined position in the heat holding zone 30 by use of the steel sheet temperature decreasing pattern stored in advance in the storage unit 111 or the like and information regarding the installation position of the radiation thermometers 50 or information that can be converted into the installation positions (step S103). This estimating processing of the steel sheet temperature is, as described above, temperature estimating processing considering the steel sheet temperature decrease in the heat holding zone. When the estimated steel sheet temperature $T(z)$ is calculated from each pieces of radiance information measured by the radiation thermometers 50 provided at the respective positions in the heat holding zone 30, the steel sheet temperature estimating unit 103 outputs the calculated plurality of estimated steel sheet temperatures to the emissivity calculating unit 105.

Subsequently, the emissivity calculating unit 105 calculates the emissivity at a predetermined position in the heat holding zone 30 by use of the radiance information transmitted from the radiance information acquiring unit 101 and the estimated steel sheet temperature notified from the steel sheet temperature estimating unit 103 (step S105). When the calculation of the emissivity ends, information regarding the calculated emissivity is output to the alloyed position determining unit 107.

Next, the alloyed position determining unit 107 determines a position where the galvannealed layer is alloyed in the heat holding zone by use of the predetermined threshold value and the information regarding the emissivity transmitted from emissivity calculating unit 105. By performing processing according to such a flow, in the alloyed position determining method according to this embodiment, it is possible to precisely determine the position where the galvannealed layer is alloyed.

(Regarding Hardware Configuration)

Figure 13:
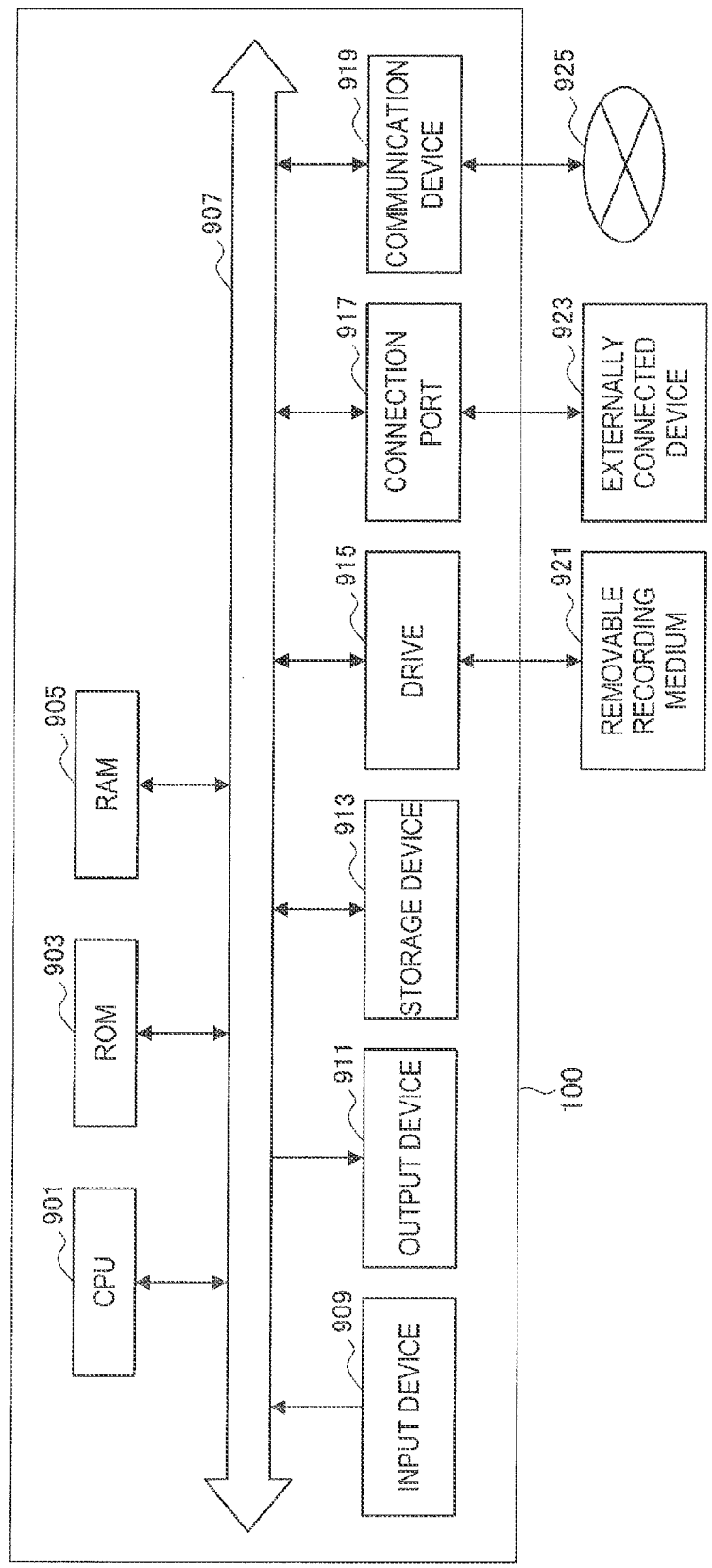
FIG. 13 is a block diagram showing a hardware configuration of an alloyed position determining apparatus according to an embodiment of the present invention.

Next, a hardware configuration of the alloyed position determining apparatus 100 according to an embodiment of the present invention will be described in detail with reference to FIG. 13. FIG. 13 is a block diagram for explaining the hardware configuration of the alloyed position determining apparatus 100 according to the embodiment of the present invention.

The alloyed position determining apparatus 100 mainly includes a CPU 901, ROM 903, and RAM 905. Furthermore, the alloyed position determining apparatus 100 also includes a bus 907, an input device 909, an output device 911, a storage device 913, drive 915, a connection port 917, and a communication device 919.

The CPU 901 serves as an arithmetic processing apparatus and a control vice, and controls the overall operation or a part of the operation of the alloyed position determining apparatus 100 according to various programs recorded in the ROM 903, the RAM 905, time storage device 913, or a removable recording medium 921. The ROM 903 stores programs, operation parameters, and the like used by the CPU 901. The RAM 905 primarily stores programs used by the CPU 901 and parameters and the like varying as appropriate during the execution of the programs. These are connected to each other via the bus 907 configured from an internal bus such as a CPU bus or the like.

The bus 907 is connected to an external bus such as a PCI (Peripheral Component Interconnect/Interface) bus via a bridge.

The input device 909 is an operation means operated by a user, such as a mouse, a keyboard, a touch panel, buttons, a switch, and a lever. Also, the input device 909 may be a remote control means (a so-called remote control) using, for example, infrared light or other radio waves, or may be an externally connected device 923 such as a PDA conforming to the operation of the alloyed position determining apparatus 100. Furthermore, the input device 909 generates an input signal based on, for example, information which is input by a user with the above operation means, and is configured from an input control circuit for outputting the input signal to the CPU 901. The user of the alloyed position determining apparatus 100 can input various data to the alloyed position determining apparatus 100 and can instruct processing by operating this input device 909.

The output device 911 is configured from a device capable of visually or audibly notifying acquired information to a user. Examples of such a device include display devices such as a CRT display device, a liquid crystal display device, a plasma display device, an EL display device, and a lamp, audio output devices such as a speaker and a headphone, a printer, a mobile phone, a facsimile machine, and the like. For example, the output device 911 outputs the results obtained by various processes performed by the alloyed position determining apparatus 100. More specifically, the display device displays the results obtained by various processes performed by the alloyed position determining apparatus 100 in the form of texts or images. On the other hand, the audio output device converts an audio signal such as reproduced audio data and sound data into an analog signal, and outputs the analog signal.

The storage device 913 is a device for storing data configured as an example of a storage unit of the alloyed position determining apparatus 100. The storage device 913 is configured from, for example, a magnetic storage device such as an HDD (Hard Disk Drive), a semiconductor storage device, an optical storage device, or a magneto-optical storage device. This storage device 913 stores programs to be executed by the CPU 901, various data, and various data obtained from the outside.

The drive 915 is a reader/writer for a recording medium, and is embedded in the alloyed position determining apparatus 100 or attached externally thereto. The drive 915 reads information recorded in the attached removable recording medium 921 such as a magnetic disk, an optical disk, a magneto-optical disk, or semiconductor memory, and outputs the read information to the RAM 905. Furthermore, the drive 915 can write record in the attached removable recording medium 921 such as a magnetic disk, an optical disk, a magneto-optical disk, or semiconductor memory. The removable recording medium 921 is, for example, a CD medium, a. DVD medium, or a Blu-ray medium. The removable recording medium 921 may be a CompactFlash (CF; registered trademark), flash memory, an SD memory card (Secure Digital memory card), or the like. Alternatively, the removable recording medium 921 may be, for example, an IC card (Integrated Circuit card) equipped with a non-contact IC chip or an electronic appliance.

The connection port 917 is a port for allowing devices to directly connect to the alloyed position determining apparatus 100. Examples of the connection port 917 include a USB (Universal Serial Bus) port, an IEEE1394 port, an SCSI (Small Computer System Interface) port, an RS-232C port, and the like. By the externally connected device 923 connecting to this connection port 917, the alloyed position determining apparatus 100 directly obtains various data from the externally connected device 923 and provides various data to the externally connected device 923.

The communication device 919 is a communication interface configured from, for example, a communication device for connecting to a communication network 925. The communication device 919 is, for example, a wired or wireless LAN (Local Area Network), Bluetooth (registered trademark), a communication card for WUSB (Wireless USB), or the like. Alternatively, the communication device 919 may be a router for optical communication, a router for ADSL (Asymmetric Digital Subscriber Line), a modem for various communications, or the like. This communication device 919 can transmit and receive signals and the like in accordance with a predetermined protocol such as TCP/IP on the Internet and with other communication devices, for example. The communication network 925 connected to the communication device 919 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the alloyed position determining apparatus 100 according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out this embodiment.

EXAMPLE

Hereinafter, the results when radiation thermometers were installed in a radiance measuring area in an actual hot dip galvanizing line and the alloyed position determining method according to an embodiment of the present invention is applied will be described specifically. Note that a specific example shown below is an example of the alloyed position determining method according to the embodiment of the present invention, and the alloyed position determining method according to the present invention is not limited to the following example.

Figure 14:
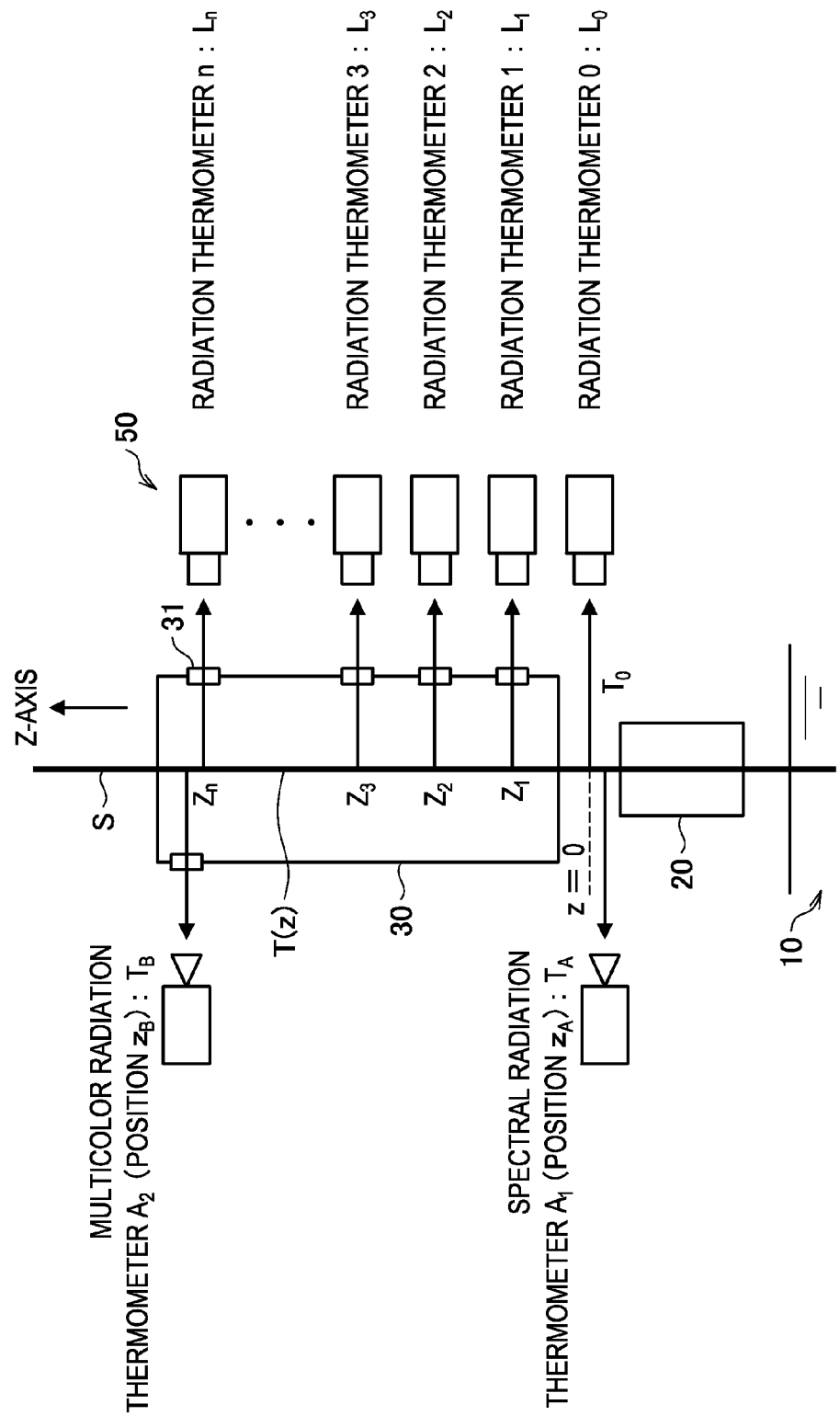
FIG. 14 is an explanatory vies for explaining a method for calculating a temperature decreasing pattern.

In the Example shown below; in addition to the radiation thermometers each used as a radiance measuring means to determine an alloyed position, in order to calculate a temperature decreasing pattern of a steel sheet, a spectral radiation thermometer $A_1$ and a multicolor radiation thermometer $A_2$ were installed in the vicinity of the hot dip galvanizing line (i.e., in the radiance measuring area) as shown in FIG. 14.

The spectral radiation thermometer refers to a radiation thermometer where the radiance is measured in one wavelength region, and is used when the emissivity of a target is not changed during measurement. Further, the multicolor radiation thermometer refers to a radiation thermometer where the radiance is measured in a plurality of wavelength regions, and can measure surface temperature even when the emissivity is changed.

Since zinc exists alone on surfaces of the steel sheet conveyed in the hot clip galvanizing line immediately after the alloying furnace 20, it is possible to measure the steel sheet temperature with the radiation thermometer (spectral radiation thermometer) with the emissivity $\epsilon$ of about 0.17. Further, since the emissivity varies in accordance with the progress of alloying in an upper part of the heat holding zone 30, it is possible to measure the steel sheet temperature with a multicolor radiation thermometer (e.g., two-color thermometer).

Here, as shown in FIG. 14, the steel sheet temperature is measured by installing the spectral radiation thermometer $A_1$ immediately after the alloying furnace 20 (at a position $z_A$) and installing the multicolor radiation thermometer $A_2$ in the upper part of the heat holding zone 30 (at a position $z_B$). When the steel sheet temperature measured with the spectral radiation thermometer $A_1$ is referred to as $T_A$ and the steel sheet temperature measured with the multicolor radiation thermometer $A_2$ is referred to as $T_B$, the steel sheet temperature in the heat holding zone 30 can be represented by the following expression 151 by linear interpolation in accordance with the height of the installed radiation thermometer.

[Math 4]

$$T(z) = T_A + \frac{T_B - T_A}{z_B - z_A}(z - z_A) \qquad \text{(Expression 151)}$$

Here, as described above, the higher the position is in the heat holding zone 30, the lower the steel sheet temperature becomes; therefore, $(T_B - T_A) < 0$ is satisfied in the expression 151. Accordingly, it is found that the expression represented by the expression 151 can be used as the temperature decreasing pattern used for estimating the degree to which the steel sheet temperature is decreased at a position z in the heat holding zone, the steel sheet temperature being $T_A$ on the entry section of the heat holding zone 30.

Example 1

States of installation of each thermometer used for measurement in the following Example will be described in detail with reference to FIG. 15.

Figure 15:
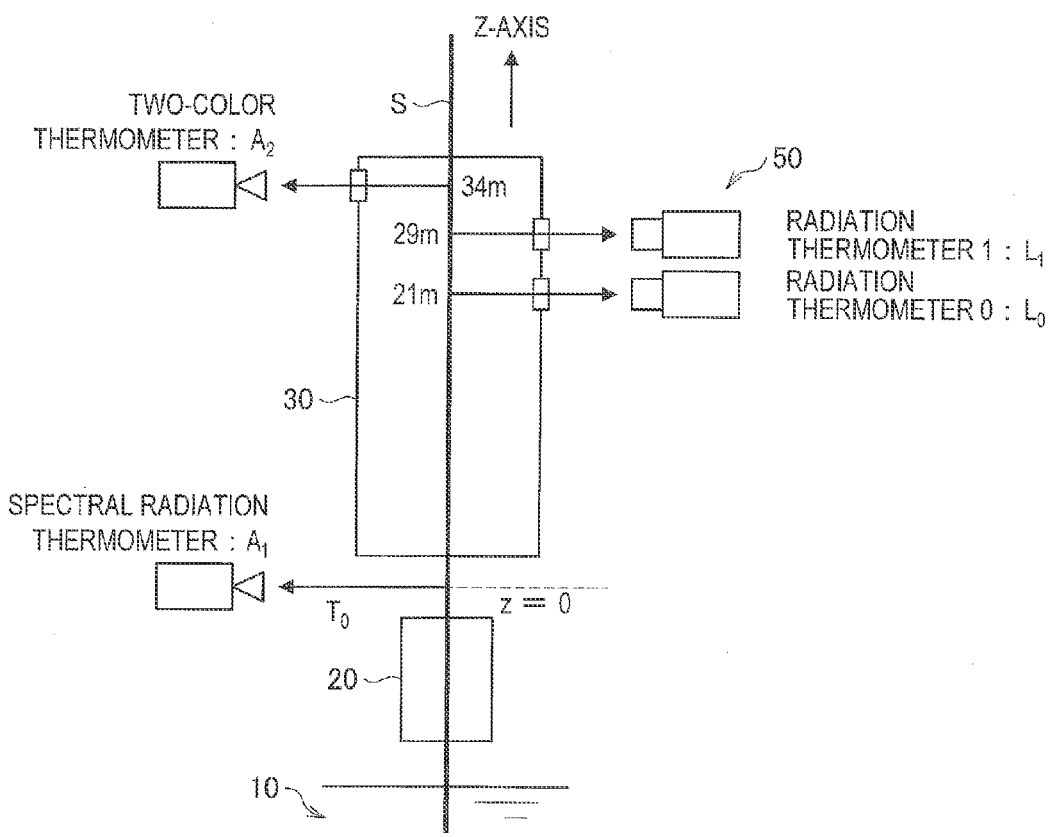
FIG. 15 is an explanatory view for explaining thermometers installed in a hot dip galvanizing line in Example 1 of the present invention.

As shown in FIG. 15, in the hot dip galvanizing line for experiment, the spectral radiation thermometer $A_1$ was installed on an delivery section (z=0) of the alloying furnace, and the two-color thermometer $A_2$ was installed in the upper part (z=34 m) in the heat holding zone. Further, two radiation thermometers were installed at positions where z=21 m and z=29 m, respectively.

In the following description, the temperature decreasing pattern of the steel sheet was calculated by use of measured temperatures obtained from the spectral radiation thermometer $A_1$ and the two-color thermometer $A_2$, and the temperature decreasing pattern was used to estimate the steel sheet temperature in the heat holding zone.

Further, for the radiation thermometers installed at z=21 m and z=29 m, the emissivity $\epsilon$ was set to 1, and these radiation thermometers were used to measure the steel sheet conveyed in the heat holding zone. That is, in this Example, these two radiation thermometers were set to output pseudo temperatures (black body temperatures at r=1) by converting observed values of radiance into the pseudo temperatures. The output values correspond to the value of $L_z$ shown in the expression 104.

Accordingly, the radiance information acquiring unit 101 executes processing for converting the pseudo temperature information output from the radiation thermometers into radiance information by use of the following expression 152.

[Math 5]

$$L_n = \frac{c_1}{\lambda^5} \cdot \frac{1}{\exp\left(\frac{c_2}{\lambda T'(z)}\right) - 1} \qquad \text{(Expression 152)}$$

Here, in the expression 152, $L_n$ is the radiance at z=21 m or z=29 m, and T'(z) is temperature information output from the radiation thermometer installed at z=21 m or z=29 m.

Further, in the expression 152, $c_1$ and $c_2$ are constants shown in the expression 102 and the expression 103, respectively, and $\lambda$ is a measured wavelength the value of which is 1.55 µm.

The steel sheet serving as a measurement target was mild steel with a sheet thickness of 1.4 mm and a sheet width of 1350 mm. This steel sheet was conveyed at a line steed of 90 mpm through the hot dip galvanizing line where the above-described thermometers were installed.

Figure 16:
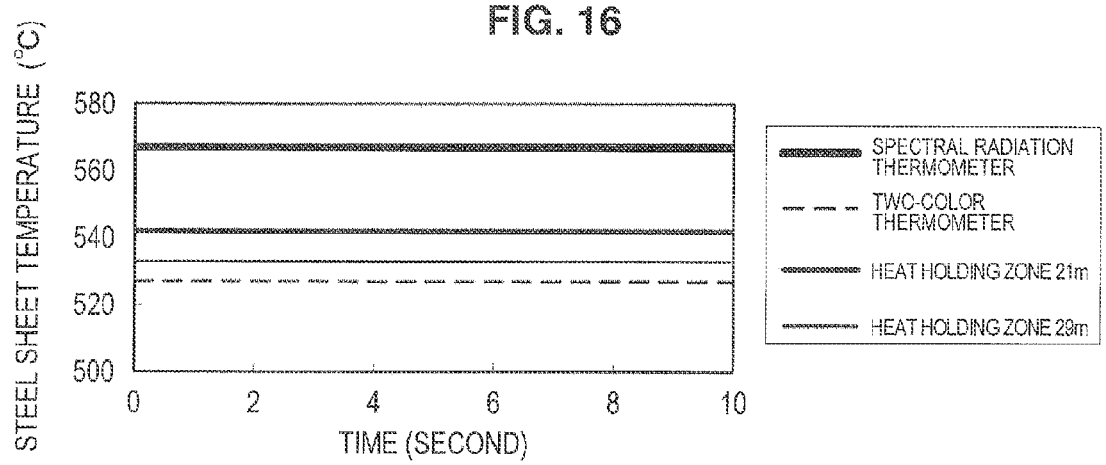
FIG. 16 is a graph showing measured values of steel sheet temperatures with a spectral radiation thermometer and a two-color thermometer and estimated steel sheet temperatures at installation positions of radiation thermometers.

FIG. 16 shows steel sheet temperatures measured with the two thermometers (the spectral radiation thermometer $A_1$ and the two-color thermometer $A_2$) together with estimated steel sheet temperatures at positions of 21 m and 29 m, which were calculated based on the obtained steel sheet temperatures.

As shown in FIG. 16, the steel sheet temperature on the delivery section of the alloying furnace was 567° C. and the steel sheet temperature at the position of 34 m in the heat holding zone was 527° C. Further, the steel sheet temperatures at the position of 21 m and at the position of 29 m were calculated to be 542° C. and 533° C., respectively, based on the expression 151 by use of the above measurement results.

Figure 17:
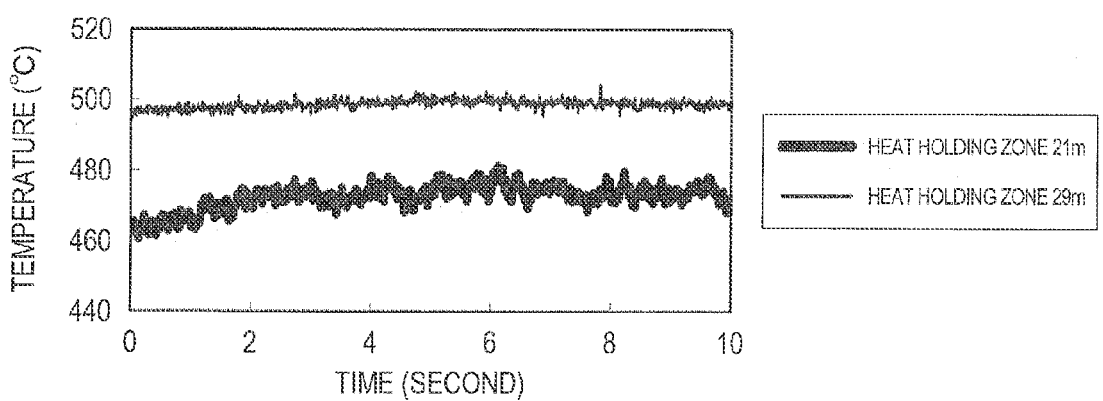
FIG. 17 is a graph showing measured values (temperature converted values when emissivity is 1) with radiation thermometers.

Further, the measured values (these values correspond to the value Lz in the expression 104) measured by the radiation thermometers at the positions of 21 m and 29 m in the heat holding zone are shown in FIG. 17. In this Example, the emissivity $\epsilon$ of each of the radiation thermometers installed at the above positions was set to 1, and the measured values were pseudo temperatures at $\epsilon=1$.

Radiance information was calculated from the expression 152 by use of the measured values by the radiation thermometers shown in FIG. 17, and emissivity was calculated based on the expression 101 by use of the calculated radiance information $L_n$ and the estimated steel sheet temperature $T(z)$ shown in FIG. 16. The thus obtained values of emissivity are shown in FIG. 18.

Figure 18:
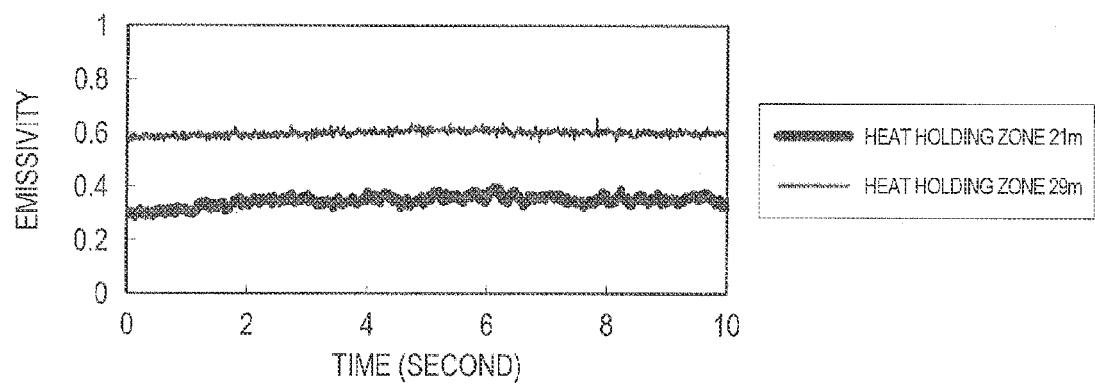
FIG. 18 is a graph showing emissivity calculated from steel sheet temperatures and radiance.

Referring to FIG. 18, the emissivity is 0.28 to 0.38 at the position of 21 m, which shows that the steel sheet has an unalloyed layer on the assumption that the alloying threshold value is 0.4. On the other hand, the emissivity is 0.6 and is almost constant at the position of 29 m, and it is found that the alloying is completed at this position. From these results, the alloyed position can be determined to be between 21 m and 29 m.

As described above, according to the alloyed position determining method and alloyed position determining apparatus each according to an embodiment of the present invention, the steel sheet temperature is estimated considering a decrease in steel sheet temperature in a heat holding zone and the steel sheet temperature obtained by the estimation is used to calculate emissivity; therefore, the emissivity can be calculated more precisely. Accordingly, even in processes using an alloying furnace such as an induction heater, which have been becoming more common in recent years, an alloyed position can be determined more precisely. As a result, by use of information regarding the alloyed position, it is possible to control the applied amount of induction heating and sheet-conveying speed in the alloying furnace such as an induction, and to perform operation so that alloying can be stable, and it is possible to prevent generation of defective quality called an unalloyed layer or an overalloyed layer.

Heretofore, preferred embodiments of the present invention have been described in detail with reference to the appended drawings, but the present invention is not limited thereto. It should be understood by those skilled in the art that various changes and alterations may be made without departing from the spirit and scope of the appended claims.

REFERENCE SIGNS LIST

1 hot dip galvanizing line
10 zinc bath
20 alloying furnace
30 heat holding zone
40 cooling zone
50 radiation thermometer
100 alloyed position determining apparatus
101 radiation information acquiring unit
103 steel sheet temperature estimating unit
105 emissivity calculating unit
107 alloyed position determining unit
109 display controlling unit
111 storage unit

The invention claimed is:

1. An alloyed position determining method comprising:
a step for measuring, by each of a plurality of radiation thermometers, radiance of a steel sheet at positions at which the radiation thermometers are installed, the radiation thermometers being installed along a conveying direction of the steel sheet in a heat holding zone in a hot dip galvanizing line of the steel sheet, the radiation thermometers measuring radiance of the steel sheet conveyed;
a radiance information acquiring step for acquiring, by a processor, information regarding a result of the measurement of radiance from each of the plurality of radiation thermometers;
a steel sheet temperature estimating step for estimating, by the processor, steel sheet temperatures at the installation positions of the radiation thermometers by use of information regarding a temperature decreasing pattern of the steel sheet, accompanied by a position change in the conveying direction in the heat holding zone, and information regarding the installation positions of the radiation thermometers;
an emissivity calculating step for calculating, by the processor, emissivity at the installation positions of the radiation thermometers by use of the estimated steel sheet temperatures estimated at the installation positions of the radiation thermometers and the information regarding the result of measurement of radiance; and
an alloyed position determining step for determining, by the processor, an alloyed position of the steel sheet in the heat holding zone based on the calculated emissivity;
wherein the information regarding the temperature decreasing pattern indicates a relationship between the installation positions of the radiation thermometers and a rate of temperature decrease, and is one of information stored in a storage unit for each manufacturing condition on the basis of past performance data or information in which results of heat transfer model simulation regarding extracted heat from the steel sheet due to an atmosphere in a furnace and an inner wall is stored in a storage unit.

2. The alloyed position determining method according to claim 1, wherein, in the steel sheet temperature estimating step, an amount of temperature decrease in the steel sheet is calculated based on the information regarding the temperature decreasing pattern of the steel sheet and the information regarding the installation positions of the radiation thermometers, and the estimated steel sheet temperatures are calculated by subtracting the calculated amount of temperature decrease from a temperature of the steel sheet on an entry section of the heat holding zone.

3. The alloyed position determining method according to claim 2, wherein, in the alloyed position determining step, when emissivity which is calculated in the emissivity calculating step and which corresponds to a position of an (n−1)(n≥2)-th radiation thermometer from the entry section of the heat holding zone is lower than a predetermined threshold value and emissivity which corresponds to a position of an n-th radiation thermometer is higher than or equal to the predetermined threshold value, it is determined that a position where alloying has occurred is a section between an installation position of an (n−1)-th radiation thermometer and an installation position of the n-th radiation thermometer in the heat holding zone.

4. The alloyed position determining method according to claim 1, wherein, in the steel sheet temperature estimating step, the temperature decreasing pattern is calculated based on a measured temperature of the steel sheet before the steel sheet enters the heat holding zone, measured with a spectral radiation thermometer, and a measured temperature of the steel sheet in the heat holding zone, measured with a multicolor radiation thermometer, and the steel sheet temperature is estimated by use of the calculated temperature decreasing pattern and the information regarding the installation positions of the radiation thermometers.

5. The alloyed position determining method according to claim 4, wherein, in the alloyed position determining step, when emissivity which is calculated in the emissivity calculating step and which corresponds to a position of an (n−1)(n≥2)-th radiation thermometer from the entry section of the heat holding zone is lower than a predetermined threshold value and emissivity which corresponds to a position of an n-th radiation thermometer is higher than or equal to the predetermined threshold value, it is determined that a position where alloying has occurred is a section between an installation position of an (n−1)-th radiation thermometer and an installation position of the n-th radiation thermometer in the heat holding zone.

6. The alloyed position determining method according to claim 1, wherein, in the alloyed position determining step, when emissivity which is calculated in the emissivity calculating step and which corresponds to a position of an (n−1)(n≥2)-th radiation thermometer from the entry section of the heat holding zone is lower than a predetermined threshold value and emissivity which corresponds to a position of an n-th radiation thermometer is higher than or equal to the predetermined threshold value, it is determined that a position where alloying has occurred is a section between an installation position of an (n−1)-th radiation thermometer and an installation position of the n-th radiation thermometer in the heat holding zone.

7. An alloyed position determining apparatus comprising:
a plurality of radiation thermometers configured to be installed along a conveying direction of a steel sheet in a heat holding zone in a hot dip galvanizing line of the steel sheet, the radiation thermometers measuring radiance of the steel sheet conveyed;
a radiance information acquiring unit configured to acquire information regarding a result of measurement of radiance from each of the plurality of radiation thermometers;
a steel sheet temperature estimating unit configured to estimate steel sheet temperatures at the installation positions of the radiation thermometers by use of information regarding a temperature decreasing pattern of the steel sheet, accompanied by a position change in the conveying direction in the heat holding zone, and information regarding the installation positions of the radiation thermometers;
an emissivity calculating unit configured to calculate emissivity at the installation positions of the radiation thermometers by use of the estimated steel sheet temperatures estimated at the installation positions of the radiation thermometers, estimated by the steel sheet temperature estimating unit, and the information regarding the result of measurement of radiance; and
an alloyed position determining unit configured to determine an alloyed position of the steel sheet in the heat holding zone based on the emissivity calculated by the emissivity calculating unit,
wherein the information regarding the temperature decreasing pattern indicates a relationship between the installation positions of the radiation thermometers and a rate of temperature decrease, and is one of information stored in a storage unit for each manufacturing condition on the basis of past operation performance data or information in which results of heat transfer model simulation regarding extracted heat from the steel sheet due to an atmosphere in a furnace and an inner wall is stored in a storage unit.

8. The alloyed position determining apparatus according to claim 7, wherein the steel sheet temperature estimating unit calculates an amount of temperature decrease in the steel sheet based on the information regarding the temperature decreasing pattern of the steel sheet and the information regarding the installation positions of the radiation thermometers, and calculates the estimated steel sheet temperatures by subtracting the calculated amount of temperature decrease from a temperature of the steel sheet on an entry section of the heat holding zone.

9. The alloyed position determining apparatus according to claim 8, wherein the alloyed position determining unit determines, when emissivity which is calculated by the emissivity calculating unit and which corresponds to a position of an (n−1)(n≥2)-th radiation thermometer from the entry section of the heat holding zone is lower than a predetermined threshold value and emissivity which corresponds to a position of an n-th radiation thermometer is higher than or equal to the predetermined threshold value, that a position where alloying has occurred is a section between an installation position of an (n−1)-th radiation thermometer and an installation position of the n-th radiation thermometer in the heat holding zone.

10. The alloyed position determining apparatus according to claim 7, wherein the steel sheet temperature estimating unit calculates the temperature decreasing pattern based on a measured temperature of the steel sheet before the steel sheet enters the heat holding zone, measured with a spectral radiation thermometer, and a measured temperature of the steel sheet in the heat holding zone, measured with a multicolor radiation thermometer, and estimates the steel sheet temperature by use of the calculated temperature decreasing pattern and the information regarding the installation positions of the radiation thermometers.

11. The alloyed position determining apparatus according to claim 10, wherein the alloyed position determining unit determines, when emissivity which is calculated by the emissivity calculating unit and which corresponds to a position of an (n−1)(n≥2)-th radiation thermometer from the entry section of the heat holding zone is lower than a predetermined threshold value and emissivity which corresponds to a position of an n-th radiation thermometer is higher than or equal to the predetermined threshold value, that a position where alloying has occurred is a section between an installation position of an (n−1)-th radiation thermometer and an installation position of the n-th radiation thermometer in the heat holding zone.

12. The alloyed position determining apparatus according to claim 7, wherein the alloyed position determining unit determines, when emissivity which is calculated by the emissivity calculating unit and which corresponds to a position of an (n−1)(n≥2)-th radiation thermometer from the entry section of the heat holding zone is lower than a predetermined threshold value and emissivity which corresponds to a position of an n-th radiation thermometer is higher than or equal to the predetermined threshold value, that a position where alloying has occurred is a section between an installation position of an (n−1)-th radiation thermometer and an installation position of the n-th radiation thermometer in the heat holding zone.

13. A non-transitory computer-readable storage medium having a program stored thereon, the program having instructions for execution by a computer,
   wherein the computer is mutually communicable with a plurality of radiation thermometers installed along a conveying direction of a steel sheet in a heat holding zone in a hot dip galvanizing line of the steel sheet, the radiation thermometers measuring radiance of the steel sheet conveyed;
   wherein the instructions, when executed, cause the computer to carry out the following method of determining an alloyed position:
   a radiance information acquiring step of acquiring information regarding a result of measurement of radiance from each of the plurality of radiation thermometers;
   a steel sheet temperature estimating step of estimating steel sheet temperatures at the installation positions of the radiation thermometers by use of information regarding a temperature decreasing pattern of the steel sheet, accompanied by a position change in the conveying direction in the heat holding zone, and information regarding the installation positions of the radiation thermometers;
   an emissivity calculating step of calculating emissivity at the installation positions of the radiation thermometers by use of the estimated steel sheet temperatures estimated at the installation positions of the radiation thermometers, estimated by the steel sheet temperature estimating function, and the information regarding the result of measurement of radiance; and
   an alloyed position determining step of determining an alloyed position of the steel sheet in the heat holding zone based on the emissivity calculated by the emissivity calculating function,
   wherein the information regarding the temperature decreasing pattern indicates a relationship between the installation positions of the radiation thermometers and a rate of temperature decrease, and is one of information stored in a storage unit for each manufacturing condition on the basis of past operation performance data or information in which results of heat transfer model simulation regarding extracted heat from the steel sheet due to an atmosphere in a furnace and an inner wall is stored in a storage unit.

* * * * *